United States Patent
Sakurada

(10) Patent No.: US 9,788,715 B2
(45) Date of Patent: Oct. 17, 2017

(54) OPTOTYPE PRESENTING APPARATUS

(71) Applicant: KABUSHIKI KAISHA TOPCON, Itabashi-ku (JP)

(72) Inventor: Tomohiro Sakurada, Itabashi-ku (JP)

(73) Assignee: KABUSHIKI KAISHA TOPCON, Itabashi-ku (JP)

( * ) Notice: Subject to any disclaimer, the term of this patent is extended or adjusted under 35 U.S.C. 154(b) by 151 days.

(21) Appl. No.: 14/414,810

(22) PCT Filed: May 30, 2013

(86) PCT No.: PCT/JP2013/065076
§ 371 (c)(1),
(2) Date: Jan. 14, 2015

(87) PCT Pub. No.: WO2014/013800
PCT Pub. Date: Jan. 23, 2014

(65) Prior Publication Data
US 2015/0182110 A1    Jul. 2, 2015

(30) Foreign Application Priority Data

Jul. 19, 2012 (JP) .................................. 2012-160257

(51) Int. Cl.
 A61B 3/00   (2006.01)
 A61B 3/08   (2006.01)
 A61B 3/032  (2006.01)

(52) U.S. Cl.
CPC ............ *A61B 3/032* (2013.01); *A61B 3/0008* (2013.01); *A61B 3/0041* (2013.01); *A61B 3/08* (2013.01)

(58) Field of Classification Search
CPC ..... A61B 3/032; A61B 3/0008; A61B 3/0041; A61B 3/08

(Continued)

(56) References Cited

U.S. PATENT DOCUMENTS 6,160,901 A    12/2000  Kage
2008/0204662 A1*  8/2008  Kanazawa ............. A61B 3/032
                                                    351/243

(Continued)

FOREIGN PATENT DOCUMENTS

EP    2 095 760       9/2009
JP    60-125891 A     7/1985

(Continued)

OTHER PUBLICATIONS

International Search Report Issued Jun. 25, 2013 in PCT/JP13/065076 Filed May 30, 2013.

(Continued)

*Primary Examiner* — Bumsuk Won
*Assistant Examiner* — Grant Gagnon
(74) *Attorney, Agent, or Firm* — Oblon, McClelland, Maier & Neustadt, L.L.P.

(57) ABSTRACT

An optotype presenting apparatus that is capable of carrying out examinations accurately is provided. An optotype presenting apparatus includes a display and a controller. The display includes left eye optotype display regions and right eye optotype display regions. The left eye optotype display regions output light having a first polarization axis. The right eye optotype display regions output light having a second polarization axis orthogonal to the first polarization axis. The left eye optotype display regions and the right eye optotype display regions are alternately arranged along pixel lines. The controller is capable of displaying a plurality of optotypes selectively on the display. Further, the controller controls the display based on a type of an optotype displayed on the display to change display luminance.

19 Claims, 18 Drawing Sheets

(58) Field of Classification Search
USPC .......................................................... 351/240
See application file for complete search history.

(56) References Cited

U.S. PATENT DOCUMENTS

| | | | |
|---|---|---|---|
| 2008/0259277 | A1 | 10/2008 | Inagaki et al. |
| 2008/0316428 | A1* | 12/2008 | Oda ................... A61B 3/032 |
| | | | 351/240 |
| 2011/0075099 | A1* | 3/2011 | Kanazawa ........ A61B 3/0285 |
| | | | 351/232 |
| 2011/0304821 | A1 | 12/2011 | Tanassi et al. |

FOREIGN PATENT DOCUMENTS

| | | |
|---|---|---|
| JP | 60 171030 | 9/1985 |
| JP | 63 176407 | 11/1988 |
| JP | 2-203832 A | 8/1990 |
| JP | 7-322304 A | 12/1995 |
| JP | 09-244548 A | 9/1997 |
| JP | 10-240945 A | 9/1998 |
| JP | 2004-229999 A | 8/2004 |
| JP | 2008 264262 | 11/2008 |
| JP | 2009 207569 | 9/2009 |
| JP | 2010-82253 A | 4/2010 |
| JP | 2011-72768 A | 4/2011 |
| JP | 2011-255045 A | 12/2011 |

OTHER PUBLICATIONS

Office Action issued on Apr. 12, 2016 in Japanese Patent Application No. 2012-160257.
Office Action issued Oct. 4. 2016 in Japanese Patent Application No. 2012-160257.
Office Action issued Feb. 28, 2017, in Japanese Patent Application No. 2016-100356.
Office Action dated May 30, 2017 in Japanese Patent Application No. 2012-160257.

* cited by examiner

FIG. 2

| OPTOTYPE TYPE | DISPLAY LUMINANCE |
|---|---|
| C1 | L1 |
| C2 | L2 |
| C3 | L3 |
| ..... | ..... |
| ..... | ..... |
| Cn | Ln |

| INPUT TIME | DISPLAY LUMINANCE |
|---|---|
| T1 | L1 |
| T2 | L2 |
| T3 | L3 |
| ..... | ..... |
| ..... | ..... |
| Tn | Ln |

33a

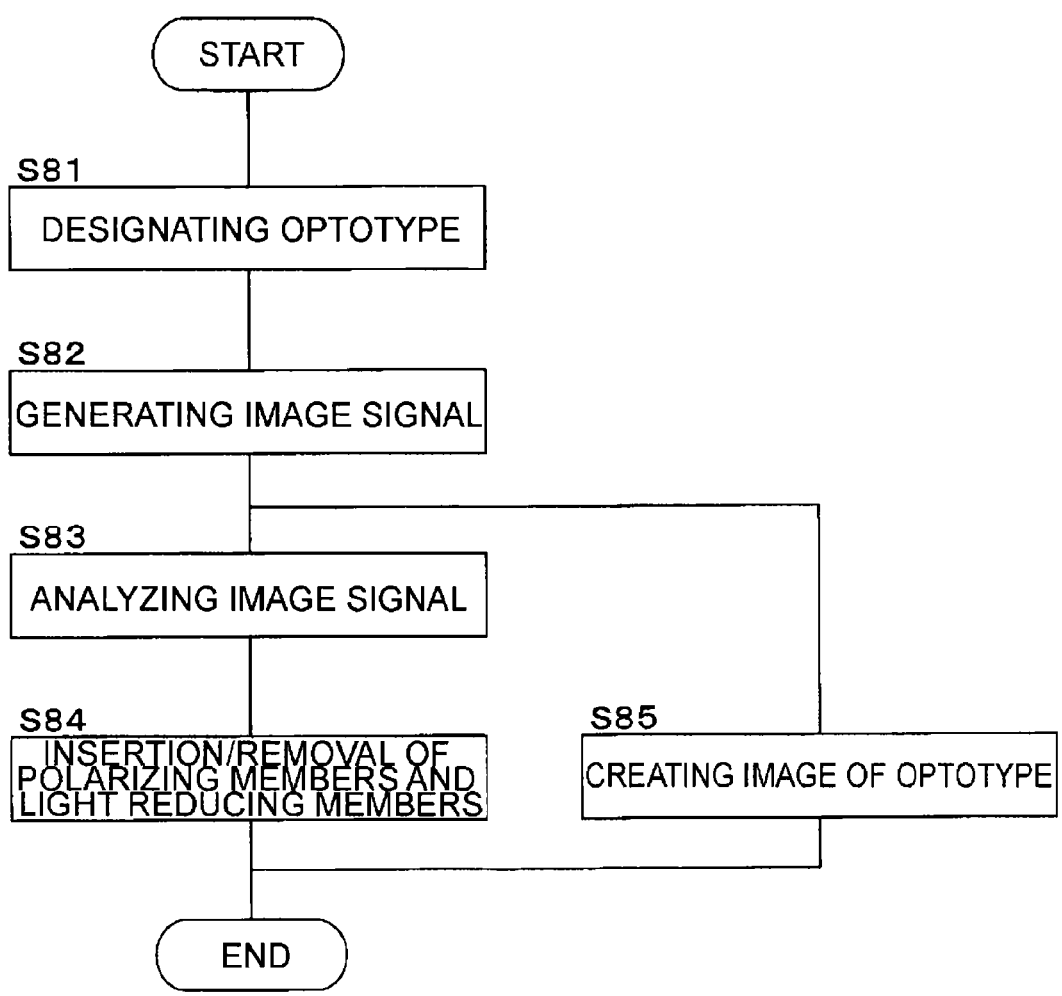

OPTOTYPE PRESENTING APPARATUS

TECHNICAL FIELD

The present invention relates to an optotype presenting apparatus used in ophthalmologic field.

BACKGROUND TECHNOLOGY

An optotype presenting apparatus is an apparatus that presents optotypes for examination of an eye. A Patent Document 1 (Japanese Laid-open Patent Publication No. 2008-148930) discloses an optotype presenting apparatus that present different optotypes to a left eye and a right eye by utilizing a display device in which polarizing films having mutually orthogonal polarization axes are alternately arranged on pixel lines and a polarizing filter that has polarization axes in accordance with these polarizing films and arranged in front of eyes to be examined. According to such an optotype presenting apparatus, it is possible to present different optotypes to the left eye and a right eye and carry out binocular visual tests and monocular tests with both eyes open.

PRIOR ART DOCUMENT

Patent Document

[Patent Document 1] Japanese Laid-open Patent Publication No. 2009-207569

SUMMARY OF THE INVENTION

Problem to be Solved by the Invention

When such a conventional optotype presenting apparatus is used, brightness of an optotype sensed by each eye is reduced by half because a display region (pixels) of the display device is divided into left eye optotype display regions and right eye optotype display regions. In addition, brightness of optotypes presented to the respective eyes is further reduced since a subject visually recognizes the optotypes through the polarizing filter. Consequently, according to such an optotype presenting apparatus, optotypes darker than usual are used in examinations, thereby causing possibility of deteriorating accuracy of examinations.

The present invention has been accomplished for the purpose of solving such a problem and the objective thereof is to provide an optotype presenting apparatus that is capable of carrying out examinations accurately.

Means for Solving the Problem

An optotype presenting apparatus of an embodiment includes: a display that includes left eye optotype display regions that output light having a first polarization axis and right eye optotype display regions that output light having a second polarization axis orthogonal to the first polarization axis, wherein the left eye optotype display regions and the right eye optotype display regions are alternately arranged along pixel lines; and a controller that is capable of displaying a plurality of optotypes selectively on the display and controls the display based on a type of an optotype displayed on the display to change display luminance.

Effect of the Invention

An optotype presenting apparatus according to the present invention is capable of carrying out examinations of eyes accurately.

BRIEF EXPLANATION OF THE DRAWINGS

FIG. 2 is a schematic diagram illustrating an example of a configuration of an optotype presenting apparatus according to an embodiment.

FIG. 6 is a schematic diagram illustrating an example of a configuration of an optotype presenting apparatus according to an embodiment.

FIG. 18 is a flowchart illustrating an example of operation of an optotype presenting apparatus according to an embodiment.

MODES FOR CARRYING OUT THE INVENTION

Figure 1:
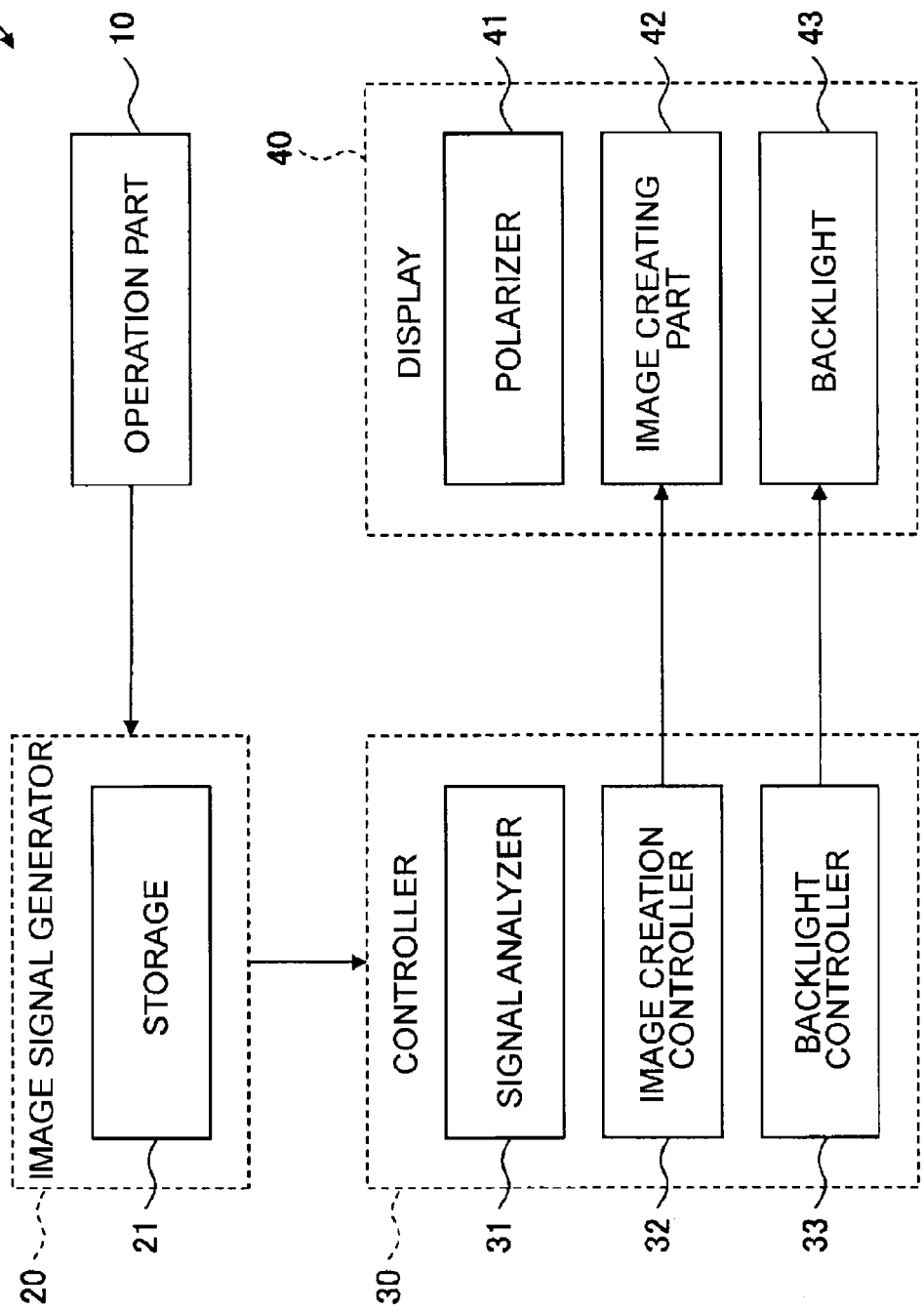
FIG. 1 is a schematic block diagram illustrating an example of a configuration of an optotype presenting apparatus according to an embodiment.

Examples of embodiments of optotype presenting apparatuses according to the present invention are explained in detail with reference to drawings. Hereinafter, first to eighth embodiments are described in order. Each of the embodiments may include similar hardware configurations to those in Patent Document 1. Any of items described in Patent Document 1 may be applied to the following embodiments.

Outline of Embodiments

To start with, the first to eighth embodiments are briefly explained. In the first to seventh embodiments, cases are described in which display luminance of an optotype is changed based on prescribed information. Here, the display luminance means brightness of display by a display device that displays optotypes.

In the first to fifth embodiments, cases are described in which display luminance of an optotype is changed in accordance with the type of the optotype presented. In the first embodiment, a case is described in which display luminance of an optotype is changed by embedding information indicating display luminance (display luminance information) in an image signal of the optotype presented (optotype presenting image signal).

In the second and third embodiments, cases are described in which display luminance is changed by using an image signal (display luminance changing image signal) other than the optotype presenting image signal. In the second embodiment, a case is described in which display luminance is changed in accordance with a time for which the display luminance changing image signal is input. In the third embodiment, a case is described in which display luminance is changed in accordance with the type of the display luminance changing image signal.

In the fourth and fifth embodiments, cases are described in which display luminance is changed by using a signal (display luminance changing signal) other than image signals. In the fourth embodiment, a case is described in which the display luminance changing signal is transmitted from an operation device receiving user's instructions (a remote controller etc.) to the display device. In the fifth embodiment, a case is described in which the display luminance changing signal is transmitted to the display device from a device that has received an operation signal from an operation device. This device has a function of generating the optotype presenting image signal.

In the sixth and seventh embodiments, cases are described in which display luminance is changed based on information other than the type of the optotype. In the sixth embodiment, a case is described in which display luminance is changed in accordance with a type of an examination (test) conducted to eyes. In the seventh embodiment, a case is described in which display luminance is changed in accordance with presence or absence of application of optical members (polarizing members) to eyes.

In the eighth embodiment, a case is described in which brightness of an optotype to be visually recognized by a subject is changed by using light reducing filters instead of changing display luminance as in the first to seventh embodiments. Use of disuse of the light reducing filters is determined on the basis of types of optotypes, types of examinations, or presence or absence of the polarizing members applied to eyes.

It should be noted that not only the first to eighth embodiments may be implemented independently but also any two or more among these may be combined. For example, any two or more among the first to seventh embodiments in which display luminance is changed may be combined. Further, any one or more among the first to seventh embodiments and the eighth embodiment may be combined.

First Embodiment

An optotype presenting apparatus of the first embodiment changes display luminance of optotypes an accordance with types of optotypes (to be) presented, and in particular, it is configured to change display luminance by embedding the display luminance information in the optotype presenting image signal.

[Configuration]

Figure 3:
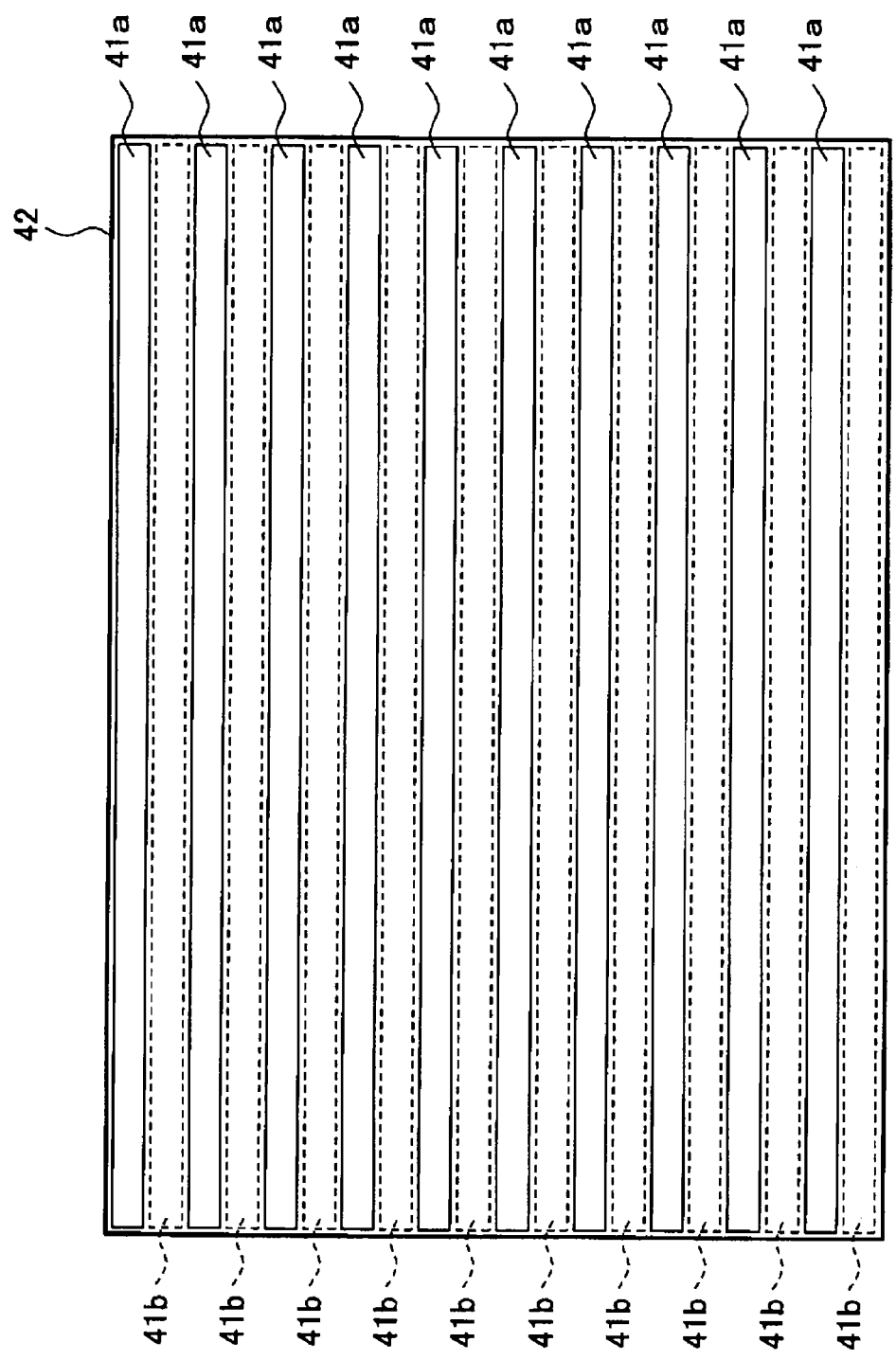
FIG. 3 is a schematic diagram illustrating an example of a configuration of an optotype presenting apparatus according to an embodiment.

FIGS. 1 to 3 illustrate an example of configuration of an optotype presenting apparatus of the present embodiment. An optotype presenting apparatus 1 includes an operation part 10, an image signal generator 20, a controller 30 and a display 40. The image signal generator 20 is provided with storage 21. The controller 30 is provided with a signal analyzer 31, an image creation controller 32 and a backlight controller 33. The display is provided with a polarizer 41, an image creating part 42 and a backlight 43.

It should be noted that the optotype presenting apparatus 1 may include an optical part (not illustrated) that applies optical members to left and right eyes of the subject. The optical members include a left eye polarizing member to be applied to the left eye and a right eye polarizing member to be applied to the right eye. A polarization axis of the left eye polarizing member is substantially parallel to a polarization axis (first polarization axis) of left eye optotype display regions described below in the polarizer 41. Similarly, a polarization axis of the right eye polarizing member is substantially parallel to a polarization axis (second polarization axis) of a right eye optotype display region described below in the polarizer 41. Here, the first polarization axis and the second polarization axis are substantially orthogonal to each other. The optical part may be configured such that optical members other than polarizing members can be applied to the eyes. As a specific example, the optical part may be configured such that a plurality of optical members is selectively applied by attaching the plurality of optical members to a rotatable turret plate. Alternatively, the optical may be a spectacle frame in which the left eye polarizing member and the right eye polarizing member are mounted.

[Operation Part]

The operation part 10 is used for operating the optotype presenting apparatus 1. The operation part 10 is provided with various buttons and switches. The buttons etc. may be hardware keys and/or software keys (graphical user interface, GUI). Upon receiving user's operation, the operation part 10 outputs a signal (operation signal) corresponding to the content of this operation. A method of communicating the operation signal may be wire communication or wireless communication.

As a specific example, the operation part 10 is provided with buttons corresponding to various types of optotypes. The user may operate a desired button to designate an optotype to be displayed by the optotype presenting apparatus 1. Upon receiving this operation, the operation part 10 transmits an operation signal indicating the type of the designated optotype to the image signal generator 20.

It should be noted that possible operations carried out by the operation part 10 are not limited to designation of an optotype. Examples of possible operations carried out by the operation part 10 include an operation of power on/off of the optotype presenting apparatus 1, an operation of designating a type of an examination to be carried out to eyes, an operation of selecting optical members to be applied to eyes by the abovementioned optical part, an operation of changing display state of the display 40, etc.

[Image Signal Generator]

The image signal generator 20 generates an image signal for displaying various types of information on the display 40. In particular, the image signal generator 20 generates an image signal for displaying an optotype (optotype presenting image signal) on the display 40. The optotype presenting image signal includes display luminance information indicating display luminance corresponding to this optotype.

In order to carry out such processing, the storage 21 of the image signal generator 20 stores image data of various types of optotypes that can be presented by the optotype presenting apparatus 1 in advance. The image data of the respective optotypes are associated with the types of the optotypes and stored. Further, the storage 21 stores optotype/display luminance associating information in which types of optotypes and display luminance are associated with each other in advance. The optotype/display luminance associating information may be table information illustrated in FIG. 2, for example. More specifically, the optotype/display luminance associating information 21a illustrated in FIG. 2 is table information configured to associate display luminance Li with types Ci of optotypes presentable by the optotype presenting apparatus 1 (i=1 to n).

Here, values of the display luminance recorded in the optotype/display luminance associating information 21a may be changed at its option. On the other hand, if the values of the display luminance are not changed or the like, it is possible to synthesize the display luminance information indicating the display luminance of a concerned optotype with the image data of this optotype in advance. If this is the case, processing of synthesizing image data and display luminance information described below is not necessary.

Display luminance relating all types of presentable optotypes is not necessarily recorded in the optotype/display luminance associating information 21a. For example, display luminance relating optotypes presented with prescribed display luminance (default value) is not necessarily recorded. Further, in a case in which only two (or more) display luminance is applied, for example, the optotype/display luminance associating information 21a may be information in which a plurality of types of optotypes (all types of optotypes, for example) is classified into these two (or more) display luminance and recorded.

Upon receiving the operation signal indicating the type of designated optotype from the operation part 10, the image signal generator 20 selectively reads out image data of the optotype corresponding to the type of optotype indicating this operation signal from the storage 21. Further, the image signal generator 20 refers to the optotype/display luminance associating information 21a to specify the display luminance corresponding to the type of optotype indicating this operation signal. Then, the image signal generator 20 synthesizes display luminance information indicating the specified display luminance with the image data of the optotype read out from the storage 21. Thereby, optotype presenting image signal including the display luminance information is generated.

Examples of optotype presenting image signal including display luminance information is described. When a blank area exist in a part of optotype presenting image signal, pixel values of pixels corresponding to at least a part of this blank area may be configured as display luminance information. Here, the blank area is an area (pixels) other than an area (pixels) constituting a optotype pattern, in other words, a background area of the optotype pattern. For example, when there is a plurality of types of values of display luminance indicated in the optotype/display luminance associating information 21a, it is possible to generate optotype presenting image signal including display luminance information by setting pixel values in accordance with values of the display luminance. Alternatively, optotype presenting image signal including display luminance information may be generated by assigning a preset pixel value to pixels, wherein the number of these pixels corresponds to the value of the display luminance. Further, it is possible to generate optotype presenting image signal including display luminance information by determining positions of pixels in a blank area to which a preset pixel value is assigned. In this example, display luminance of the optotype is set based on pixel values of the blank area.

Display luminance information is not necessarily included in optotype presenting image signal in the present embodiment. For example, when there are only two types of values of display luminance (normal luminance and high luminance) in the optotype/display luminance associating information 21a, it is possible to generate optotype presenting image signal including no display luminance information in the case of a low luminance optotype and generate optotype presenting image signal including display luminance information in the case of a high luminance optotype. In this example, display luminance is set according to presence/absence of display luminance information.

[Controller]

The optotype presenting image signal generated by the image signal generator 20 is input into the controller 30. The signal analyzer 31 of the controller 30 analyzes the optotype presenting image signal to extract the display luminance information (or to judge presence or absence of the display luminance information). The signal analyzer 31 transmits the extracted display luminance information (or information indicating presence or absence of the display luminance information) to the backlight controller 33. The backlight controller 33 controls the backlight 43 of the display 40 based on the information input from the signal analyzer 31 to realize the display luminance indicated in this display luminance information (or to realize the display luminance corresponding to presence or absence of the display luminance information).

In addition, the image creation controller 32 controls the image creating part 42 of the display 40 based on this optotype presenting image signal to cause the image creating part 42 to create the pattern of this optotype. The image creation controller 32 and the backlight controller 33 execute the above processing in parallel, for example.

At least part of the controller 30 may be provided in a display device. If this is the case, this display includes at least part of the controller 30 and the display 40. For example, when whole of the controller 30 is installed in the display device, the signal analyzer 31 includes a scaler.

[Display]

The display 40 includes, for example, a liquid crystal display (LCD), an organic electroluminescence display, etc. Upon receiving control from the image creation controller 32, the image creating part 42 creates various kinds of visual information including an optotype. The image creating part 42 is provided with a plurality of pixels arranged in a vertical and horizontal array. The backlight 43 illuminates the image creating part 42 from the back. The polarizer 41 is provided in front of the image creating part 42.

FIG. 3 is a schematic diagram of a front view of the image creating part 42 and the polarizer 41. Although illustration is omitted, the image creating part 42 includes a plurality of pixels in an array as described above. The polarizer 41 includes first polarizing regions 41a that selectively transmit light having the first polarization axis and second polarizing regions 41b that selectively transmit light having the second polarization axis orthogonal to the first polarization axis. The first polarizing regions 41a and the second polarizing regions 41b have shapes along horizontal pixel lines of the image creating part 42, and are alternately arranged in vertical-line direction. Each of the first polarizing regions 41a and the second polarizing regions 41b is configured by a polarizing film, for example. It should be noted that a method of polarization may be a direct use of linear polarization or use of circular polarization generated by a ¼ wave plate arranged in the post-stage of a member for obtaining linear polarization.

The first polarizing regions and the second polarizing regions may have shapes along vertical pixel lines of the image creating part 42 and alternately arranged in horizontal-line direction. Further, the width of each polarizing region does not necessarily correspond to one-pixel size, but may be two-pixel size, for example.

The display regions in which the first polarizing regions 41a are arranged function as an example of left eye optotype display regions that output light having the first polarization axis. Similarly, the display regions in which the second polarizing regions 41b are arranged function as an example of right eye optotype display regions that output light having the second polarization axis. It should be noted that the configuration of the display 40 is similar to conventional ones.

[Operation]

Figure 4:
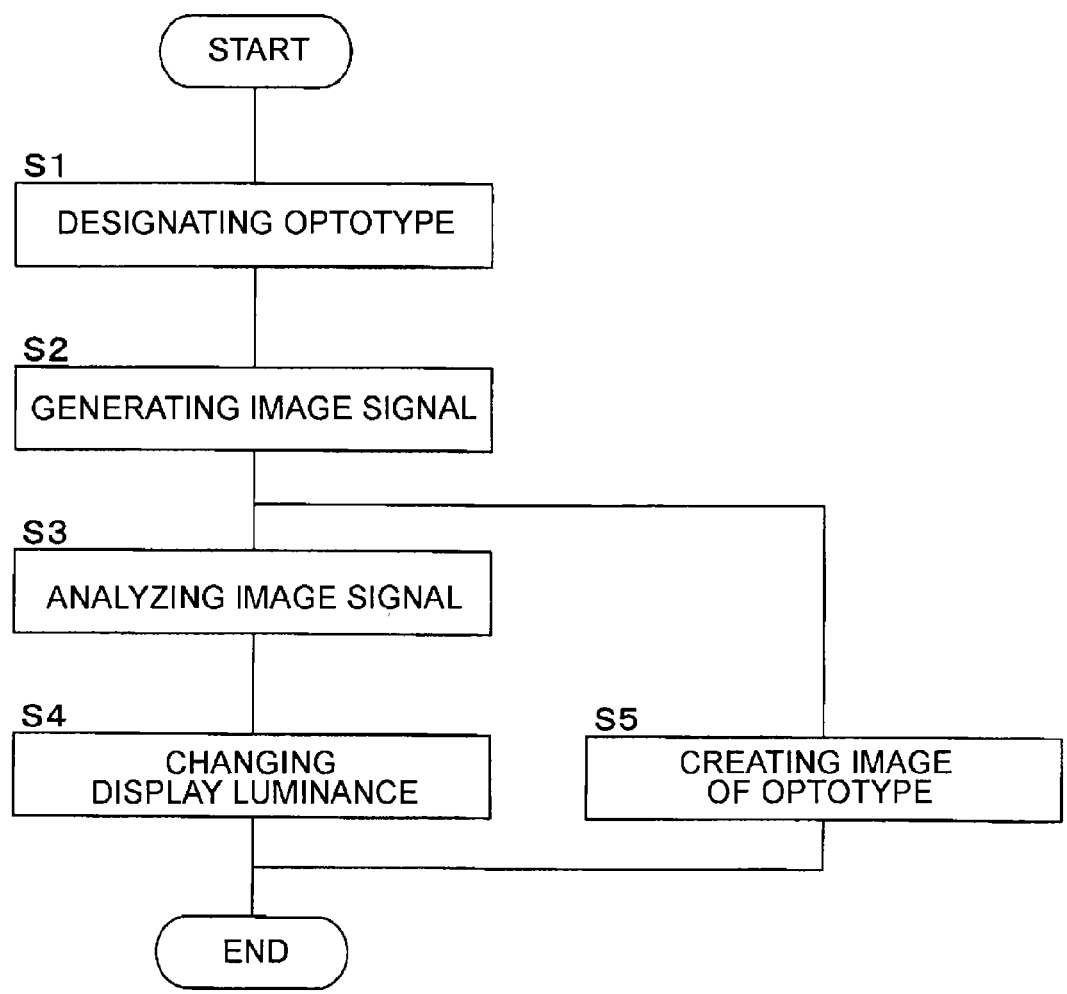
FIG. 4 is a flowchart illustrating an example of operation of an optotype presenting apparatus according to an embodiment.

Operations of the optotype presenting apparatus 1 according to the present embodiment are described. An example of an operation of the optotype presenting apparatus 1 is shown in FIG. 4.

S1: Designating Optotype

First, the user uses the operation part 10 to designate an optotype. The operation part 10 transmits an operation signal indicating the type of the designated optotype to the image signal generator 20.

S2: Generating Image Signal

The image signal generator 20 generates an optotype presenting image signal corresponding to the type of the optotype indicated by the operation signal based on the operation signal input from the operation part 10. This optotype presenting image signal includes display luminance information indicating the display luminance information corresponding to this type of the optotype. The image signal generator 20 transmits the generated optotype presenting image signal to the controller 30.

S3: Analyzing Image Signal

The image analyzer 31 analyzes the optotype presenting image signal input from the image signal generator 20 to extract the display luminance information (or to judge presence or absence of the display luminance information). The image analyzer 31 transmits the extracted display luminance information (or information indicating presence or absence of the display luminance information) to the backlight controller 33.

S4: Changing Display Luminance

The backlight controller 33 controls the backlight 43 based on the information input from the image analyzer 31 to change display luminance of the display 40.

S5: Creating Image of Optotype

While carrying out Steps 3 and 4, the image creation controller 32 controls the image creating part 42 based on the optotype presenting image signal input from the image signal generator 20 to create an image of the pattern of the optotype.

This completes processing of changing display luminance of the optotype according to the present operation example. The user performs examinations of eyes by using the optotype thus presented.

Now, specific examples of optotypes presented with high display luminance (high luminance presented optotypes) and utilization of such optotypes in visual acuity tests are described. The optotype presenting apparatus 1 according to the present embodiment is used for visual acuity tests with both eyes open. Such visual acuity tests may be monocular tests or binocular tests.

When a monocular test with both eye open is carried out, only one of the left eye optotype display regions and the right eye optotype display regions are used such that only one eye (test object) can recognize optotypes. Specifically, when a monocular test of a left eye with both eyes open, only the left eye optotype display regions are controlled to display optotypes while the right eye optotype display regions are not used. Similarly, when a monocular test of a right eye with both eyes open, only the right eye optotype display regions are controlled to display optotypes while the left eye optotype display regions are not used. The left eye optotype display regions and the right eye optotype display regions are alternately provided along pixel lines as described above and alternate pixel lines are used in such a monocular test, thereby brightness of optotypes visually recognized by a subject is reduced by half.

Examples of high luminance presented optotypes utilized in such monocular tests include the followings. In the present embodiment, the optotype/display luminance associating information 21a may be used in which display luminance corresponding to optotypes listed below is set to be high.

optotypes for visual acuity test (Landolt rings)
optotypes for visual acuity test (letter "E", referred to as an E chart)
optotypes for visual acuity test (alphabet, referred to as Snellen's optotypes)
optotypes for visual acuity test (hiragana or katakana)
optotypes for visual acuity test (numbers)
optotypes for child's visual acuity test (graphics)
optotypes for cortical vision test (Landolt rings; eye-test charts in which intervals of optotypes becomes smaller as visual acuity values increase)
optotypes for cortical vision test (alphabet; the same as above)
optotypes for red-green test (referred to as a red-green test chart)
radial-shape optotypes for astigmatism test
point-group optotypes for astigmatism test Further, optotypes are presented to both eyes in binocular examinations. In particular, when different optotypes are presented to left and right eyes (or when different images of an optotype of the same type are presented to left and right eyes), brightness of the respective optotypes visually recognized by the left and right eyes is reduced by half because the left eye optotype display regions and the right eye optotype display regions are configured as described above.

Examples of high luminance presented optotypes utilized in such binocular tests include the followings. In the present embodiment, the optotype/display luminance associating information 21a may be used in which display luminance corresponding to optotypes listed below is set to be high.
- optotypes for polarization red-green balance test
- optotypes for polarization balance test (Landolt rings)
- optotypes for polarization balance test (alphabet)
- optotypes for polarization balance test (hiragana, katakana)
- polarization cross optotypes
- polarization cross optotypes with fixation point
- polarization rotational cross optotypes with fixation point
- polarization aniseikonia optotypes (vertical notch type)
- polarization aniseikonia optotypes (horizontal notch type)
- polarization stereopsis optotypes (in which a plurality of triangles is arranged in an array)
- polarization stereopsis optotypes (in which two vertical lines are arranged above and below a center point)
- polarization stereopsis optotypes (in which a plurality of vertical lines is arranged in a rectangular frame)

[Effects]

Effects of the optotype presenting apparatus 1 of the present embodiment are explained.

The optotype presenting apparatus 1 includes the controller 30 and the display 40. The display includes the left eye optotype display regions and the right eye optotype display regions, wherein the left eye optotype display regions and the right eye optotype display regions are alternately arranged along pixel lines. The left eye optotype display regions output light having the first polarization axis. The right eye optotype display regions output light having the second polarization axis orthogonal to the first polarization axis. The controller 30 is capable of displaying a plurality of optotypes selectively on the display 40. Further, the controller 30 controls the display 40 based on a type of an optotype displayed on the display 40 to change display luminance.

According to the optotype presenting apparatus 1 thus configured, it is possible to present an optotype(s) for a left eye and an optotype for a right eye with suitable brightness (display luminance) in accordance with the type(s) of the optotype(s). Consequently, examinations of eyes may be carried out accurately. Further, since change of display luminance may be realized by using image signals for presenting optotypes, there is an advantage that one does not need to prepare extra apparatus or communication instruments.

The optotype presenting apparatus 1 may further include the image signal generator 20. The image signal generator 20 generates an image signal for displaying an optotype, wherein the image signal (optotype presenting image signal) includes display luminance information indicating display luminance corresponding to this optotype. The controller 30 is configured to display the optotype based on the generated optotype presenting image signal and executes change of display luminance based on the display luminance information included in this optotype presenting image signal.

The optotype presenting apparatus 1 may further include the operation part 10 for designating a type of an optotype to be displayed on the display 40. In this case, the operation part 10 functions as an example of an "optotype type designating part". The image signal generator 20 is configured to generate an image signal corresponding to the type of the optotype designated via the operation part 10.

The display 40 includes the image creating part 42 that creates an optotype and a backlight 43 that is provided behind the image creating part 42, for example. The controller 30 is configured to change emission intensity of the backlight 43 to execute change of display luminance.

The left eye optotype display regions may be configured by providing polarizing films that transmit light having the first polarization axis. Similarly, the right eye optotype display regions may be configured by providing polarizing films that transmit light having the second polarization axis orthogonal to the first polarization axis.

Second Embodiment

An optotype presenting apparatus according to the second embodiment performs change of display luminance by using an image signal (display luminance changing image signal) other than the optotype presenting image signal, and in particular, is configured to change display luminance in accordance with a time for which the display luminance changing image signal is input. Hereinafter, configurations and symbols in the first embodiment are applied correspondingly.

[Configuration]

An optotype presenting apparatus according to the present embodiment has configurations similar to the first embodiment (see FIGS. 1 and 3). However, contents of operations of the image signal generator 20 and the controller 30 are different from those in the first embodiment.

The image signal generator 20 of the present embodiment generates a first image signal (optotype presenting image signal) for displaying an optotype and a second image signal (display luminance changing image signal) including display luminance information indicating display luminance. Specifically, upon receiving result of designation of a type of an optotype by the operation part 10, the image signal generator 20 generates the optotype presenting image signal indicating an optotype pattern of this type of the optotype and generates the display luminance changing image signal indicating display luminance corresponding to this type of the optotype.

Figure 5:
FIG. 5 is a schematic diagram illustrating an example of a configuration of an optotype presenting apparatus according to an embodiment.

Similar to the first embodiment, the storage 21 previously stores information in which types of optotypes and image data of optotypes are associated with each other (optotype associating information) as data for executing the processing described above. Further, the storage 21 previously stores optotype/input time associating information in which types of optotypes and a time of the display luminance changing image signal input into the controller 30. The optotype/input time associating information may be table information as illustrated in FIG. 5, for example. Specifically, optotype/input time associating information 21b shown in FIG. 5 is configured as table information in which types Ci of optotypes presentable by the optotype presenting apparatus 1 and input times Ti are associated with each other (i=1 to n).

Processing of generating the optotype presenting image signal is executed by specifying image data corresponding to the designated type of optotype based on the optotype associating information. Further, processing of generating the display luminance changing image signal is executed by specifying input time corresponding to the designated type of optotype based on the optotype/input time associating information 21b. It should be noted that the display luminance changing image signal has a predetermined pattern. For example, the display luminance changing image signal may be an image signal in which pixel values of predetermined pixels are set to a value(s) other than pixel values of other pixels. The image signal generator 20 inputs the generated display luminance changing image signal into the controller 30 for the input time specified.

The image creation controller 32 of the controller 30 controls the image creating part 42 of the display 40 based on the optotype presenting image signal generated by the image signal generator 20 to display the pattern of the designated optotype.

Further, the backlight controller 33 controls the backlight 43 based on the display luminance changing image signal input from the image signal generator 20 to change display luminance. More specifically, the backlight controller 33 execute the change of display luminance based on a time of receiving input of the display luminance changing image signal from the image signal generator 20.

In order to realize such processing, the backlight controller 33 carries out change of display luminance in response to reception of the display luminance changing image signal for a preset time length continuously. This processing may be used in a case in which two display luminance are switched alternately or a case in which three or more display luminance are switched cyclically, for example. It should be noted that when this processing is applied, the optotype/input time associating information 21b is not necessarily used; alternatively, the image signal generator 20 may be configured to input the display luminance changing image signal for a preset time length, for example. Further, processing of judging whether or not the display luminance changing image signal is input (received) for a preset time length continuously is carried out by the signal analyzer 31 or the backlight controller 33 including a timer. For example, the timer starts clocking of the preset time length in response to commencement of input of the display luminance changing image signal, and it is judged whether or not the input of the display luminance changing image signal is finished before the preset time length is clocked, thereby judging whether or not the input is continued for the preset time length. It should be noted that in a case in which the signal analyzer 31 performs the clocking of the input time, the signal analyzer 31 is configured to transmit the result of clocking (or the result of judgment) to the backlight controller 33.

In another example of processing, the backlight controller 33 changes display luminance by a change amount corresponding to a time length for which the display luminance changing image signal is continuously received. In a case in which this processing is applied, the backlight controller 33 previously stores input time/display luminance associating information in which input time and display luminance are associated with each other. The input time/display luminance associating information is table information shown in FIG. 6, for example. Specifically, the input time/display luminance associating information 33a is information created in accordance with the optotype/input time associating information 21b shown in FIG. 5 and is configured as table information that associates display luminance Li with input time Ti of the display luminance changing image information from the image signal generator 20 into the controller 30 (i=1 to n). The backlight controller 33 refers to the input time/display luminance associating information 33a to specify display luminance corresponding to a input time of the display luminance changing image information from the image signal generator 20. It should be noted that in a case in which the signal analyzer 31 executes the clocking of the input time, the signal analyzer 31 is configured to transmit the result of clocking to the backlight controller 33.

[Operation]

Figure 7:
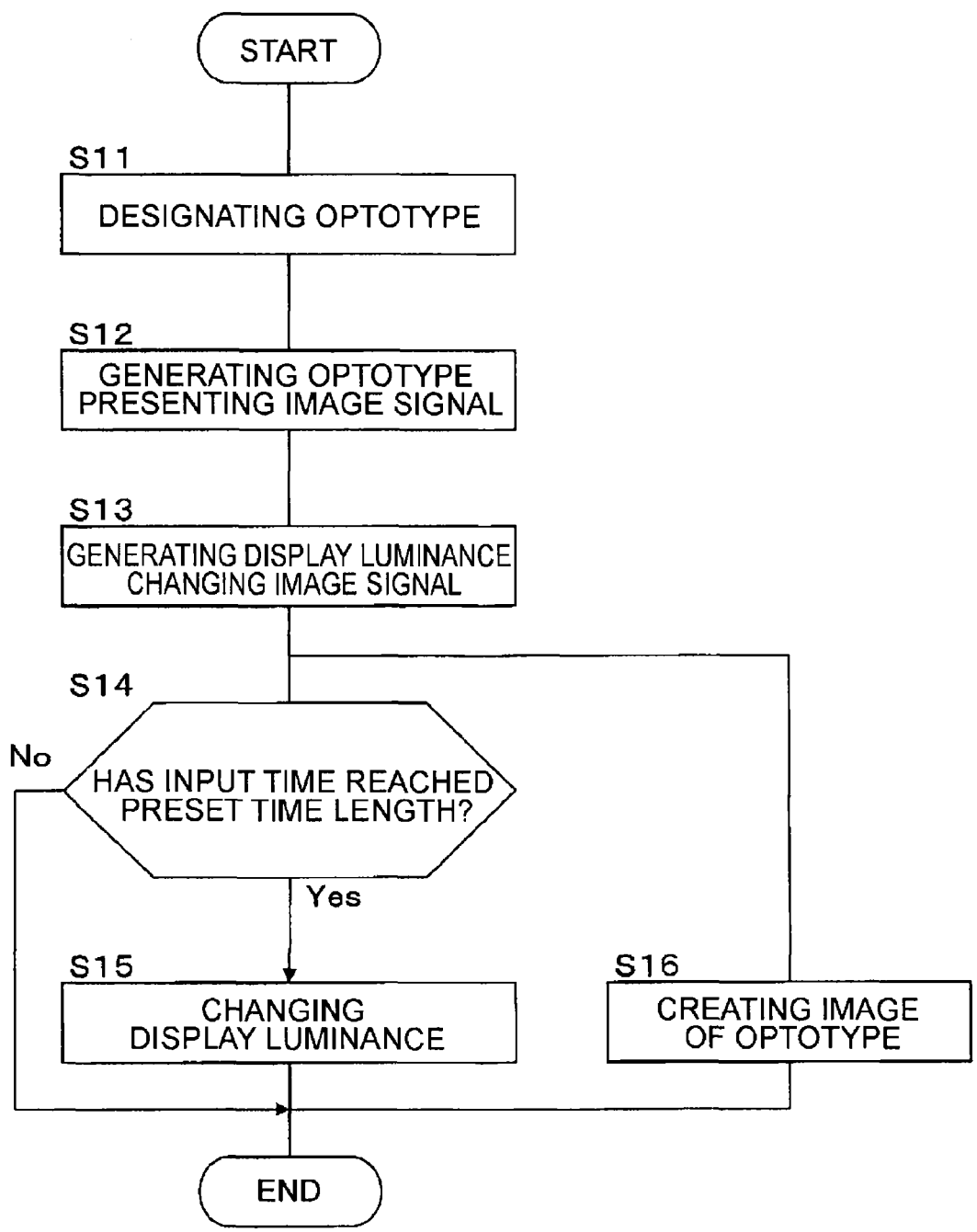
FIG. 7 is a flowchart illustrating an example of operation of an optotype presenting apparatus according to an embodiment.
Figure 8:
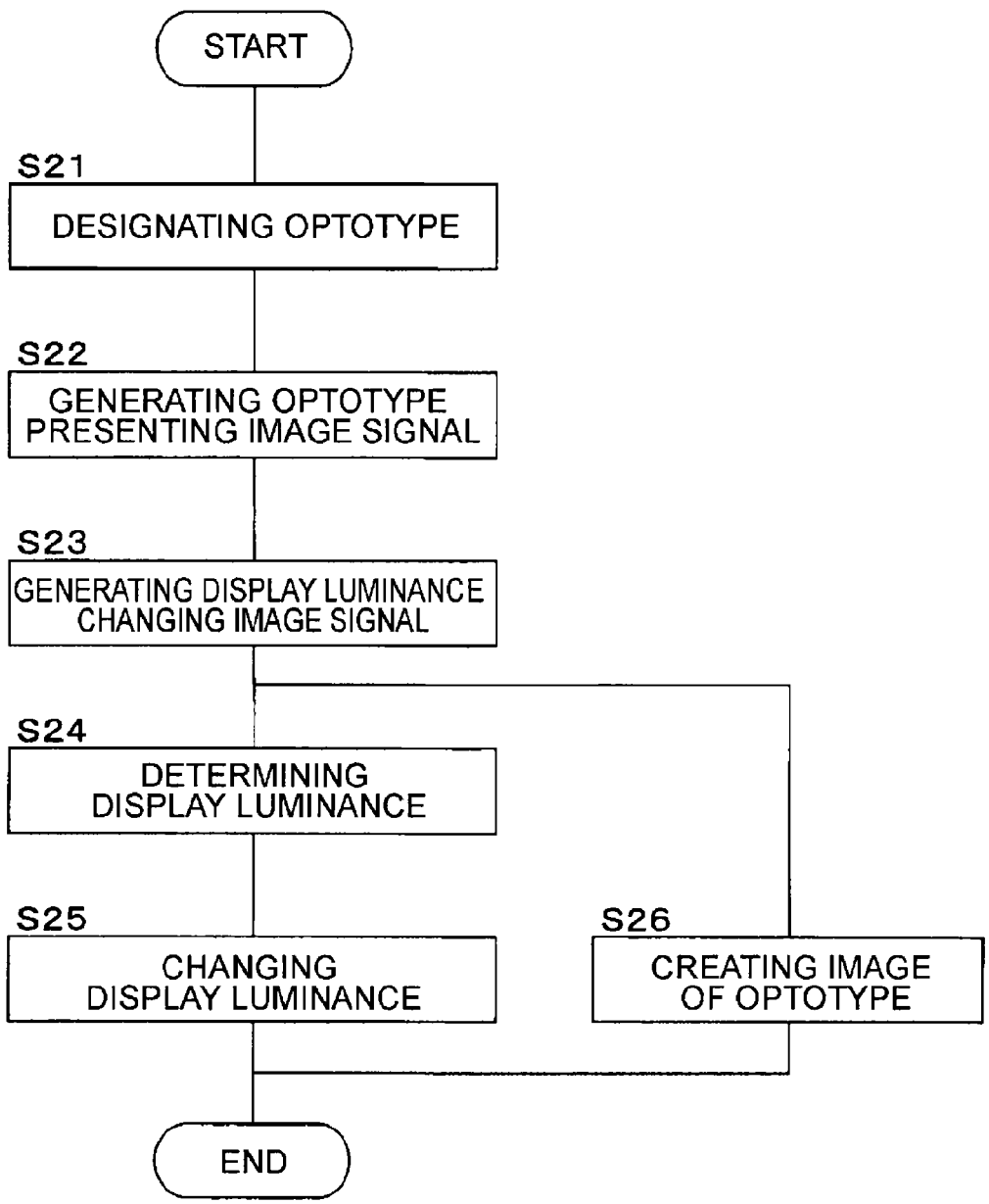
FIG. 8 is a flowchart illustrating an example of operation of an optotype presenting apparatus according to an embodiment.

Operations of the optotype presenting apparatus 1 according to the present embodiment are described. Examples of an operation of the optotype presenting apparatus 1 are shown in FIGS. 7 and 8. A first operation example shown in FIG. 7 changes display luminance in response to reception of input of the display luminance changing image information for a preset time length continuously. Further, a second operation example shown in FIG. 7 changes display luminance by a change amount corresponding to a time length for which the input of the display luminance changing image information is continued.

First Operation Example

S11: Designating Optotype

Once the user uses the operation part 10 to designate an optotype, the operation part 10 transmits an operation signal indicating the type of the designated optotype to the image signal generator 20.

S12: Generating Optotype Presenting Image Signal

The image signal generator 20 generates an optotype presenting image signal corresponding to the type of the optotype indicated by the operation signal based on the operation signal input from the operation part 10. The image signal generator 20 transmits the generated optotype presenting image signal to the controller 30.

S13: Generating Display Luminance Changing Image Signal

The image signal generator 20 generates a display luminance changing image signal corresponding to the type of the optotype indicated by the operation signal based on the operation signal input from the operation part 10. The image signal generator 20 transmits the generated display luminance changing image signal to the controller 30. It should be noted that the processing of generating the optotype presenting image signal and the processing of generating the display luminance changing image signal may be executed in parallel, or alternatively, any one of these processing may be executed after the other.

S14: Has Input Time Reached Preset Time Length?

The image analyzer 31 or the backlight controller 33 judges whether or not the input time length of the display luminance changing image signal from the image signal generator 20 has reached a preset time length.

S15: Changing Display Luminance

If it is judged that the input time length of the display luminance changing image signal has reached the preset time length (S14: Yes), the backlight controller 33 controls the backlight 43 to change display luminance of the display 40. On the other hand, if it is judged that the input time length has not reached the preset time length (S14: No), display luminance is not changed.

S16: Creating Image of Optotype

The image creation controller 32 controls the image creating part 42 based on the optotype presenting image signal input from the image signal generator 20 to create an image of the pattern of the optotype.

This completes processing of changing display luminance of the optotype according to the present operation example. The user performs examinations of eyes by using the optotype thus presented.

Second Operation Example

S21: Designating Optotype

Once the user uses the operation part 10 to designate an optotype, the operation part 10 transmits an operation signal indicating the type of the designated optotype to the image signal generator 20.

S22: Generating Optotype Presenting Image Signal

The image signal generator 20 generates an optotype presenting image signal corresponding to the type of the optotype indicated by the operation signal based on the operation signal input from the operation part 10. The image signal generator 20 transmits the generated optotype presenting image signal to the controller 30.

S23: Generating Display Luminance Changing Image Signal

The image signal generator 20 generates a display luminance changing image signal corresponding to the type of the optotype indicated by the operation signal based on the operation signal input from the operation part 10. The image signal generator 20 transmits the generated display luminance changing image signal to the controller 30 for an input time length specified based on the optotype/input time associating information 21b. It should be noted that the processing of generating the optotype presenting image signal and the processing of generating the display luminance changing image signal may be executed in parallel, or alternatively, any one of these processing may be executed after the other.

S24: Determining Display Luminance

The image analyzer 31 or the backlight controller 33 determines display luminance corresponding to the input time length of the display luminance changing image signal from the image signal generator 20 based on the input time/display luminance associating information 33a.

S25: Changing Display Luminance

The backlight controller 33 controls the backlight 43 based on the display luminance determined in Step S24 to change display luminance of the display 40 to the determined display luminance.

S26: Creating Image of Optotype

The image creation controller 32 controls the image creating part 42 based on the optotype presenting image signal input from the image signal generator 20 to create an image of the pattern of the optotype.

This completes processing of changing display luminance of the optotype according to the present operation example. The user performs examinations of eyes by using the optotype thus presented.

[Effects]

Effects of the optotype presenting apparatus 1 of the present embodiment are explained. It should be noted that the present embodiment includes configurations similar to the first embodiment and any combination thereof and these cause effects similar to the first embodiment (the same applies to the third to eight embodiments).

Unlike the first embodiment in which the optotype presenting image signal including display luminance information is generated, the image signal generator 20 of the present embodiment generates two kinds of image signals, namely the optotype presenting image signal and the display luminance changing image signal, separately. Then, the controller 30 displays the optotype on the display 40 based on the generated optotype presenting image signal and changes display luminance of the display 40 based on the display luminance changing image signal.

According to the optotype presenting apparatus 1 thus configured, it is possible to present an optotype(s) for a left eye and an optotype for a right eye with suitable brightness (display luminance) in accordance with the type(s) of the optotype(s). Consequently, examinations of eyes may be carried out accurately.

The controller 30 may change display luminance based on the input time of the display luminance changing image signal. As a specific example thereof, the controller 30 may change display luminance in response to the fact that the display luminance changing image signal is continuously input for a preset period of time (preset time length). Alternatively, the controller 30 may change display luminance by a change amount corresponding to the period of time (time length) for which the display luminance changing image signal is continuously input.

It should be noted that the operation example shown in FIG. 7 changes display luminance in response to the fact that the display luminance changing image signal is continuously input for a preset time length. Here, it may be configured to carry out different processing when the input is continued for the preset time length and when not continued. For example, regarding a configuration capable of switching display luminance between high luminance and low luminance, it is possible to control such so as to switch display luminance to high luminance when the input is continued for a preset time length and switch to low luminance when not continued.

The optotype presenting apparatus 1 further includes the operation part 10 for designating a type of an optotype to be displayed on the display 40. In this case, the operation part 10 functions as an example of the "optotype type designating part". The image signal generator 20 is configured to generate an image signal corresponding to the type of the optotype designated using the operation part 10.

Third Embodiment

An optotype presenting apparatus according to the third embodiment performs change of display luminance by using an image signal (display luminance changing image signal) other than the optotype presenting image signal, and in particular, is configured to change display luminance in accordance with the type of the display luminance changing image signal. Hereinafter, configurations and symbols in the first and second embodiments are applied correspondingly.

[Configuration]

An optotype presenting apparatus according to the present embodiment has configurations similar to the first embodiment (see FIGS. 1 to 3). However, contents of operations of the image signal generator 20 and the controller 30 are different from those in the first and second embodiments.

The image signal generator 20 of the present embodiment generates an optotype presenting image signal and a display luminance changing image signal separately as in the second embodiment. Specifically, upon receiving result of designation of a type of an optotype by the operation part 10, the image signal generator 20 generates the optotype presenting image signal indicating an optotype pattern of this type of the optotype and generates the display luminance changing image signal indicating display luminance corresponding to this type of the optotype.

As data for executing such processing, the storage 21 previously stores optotype associating information in which types of optotypes and image data of optotypes are associated with each other and the optotype/display luminance associating information 21a. The optotype/display luminance associating information 21a has a configuration similar to the first embodiment, for example (see FIG. 2).

Processing of generating the optotype presenting image signal is executed by specifying image data corresponding to the designated type of optotype based on the optotype associating information.

Processing of generating the display luminance changing image signal is executed by specifying display luminance corresponding to the designated type of optotype based on the optotype/display luminance associating information 21a. Thereby, different types of display luminance changing image signals are generated in accordance with the types of optotypes. In other words, the display luminance changing image signal has a pattern in accordance with the value of the display luminance specified. For example, it is possible to determine pixel values of predetermined pixels according to the value of the display luminance, thereby generating the display luminance changing image signal. Alternatively, it is possible to determine pixels (addresses) based on the value of the display luminance and setting a pixel value(s) to these pixels different form pixel values of other pixels, thereby generating the display luminance changing image signal.

The controller 30 displays an optotype based on the optotype presenting image signal generated by the image signal generator 20 and changes display luminance based on the type of the display luminance changing image signal. For example, the controller 30 changes display luminance by a change amount corresponding to the type of the display luminance changing image signal.

In order to realize such processing, the signal analyzer 31 or the backlight controller 33 previously stores signal type/display luminance associating information in which types of display luminance changing image signals (for example, pixel values of predetermined pixels, addresses of pixels, etc.) and display luminance. The signal analyzer 31 or the backlight controller 33 refers to the signal type/display luminance associating information to specify display luminance corresponding to the type of the display luminance changing image signal.

[Operation]

Figure 9:
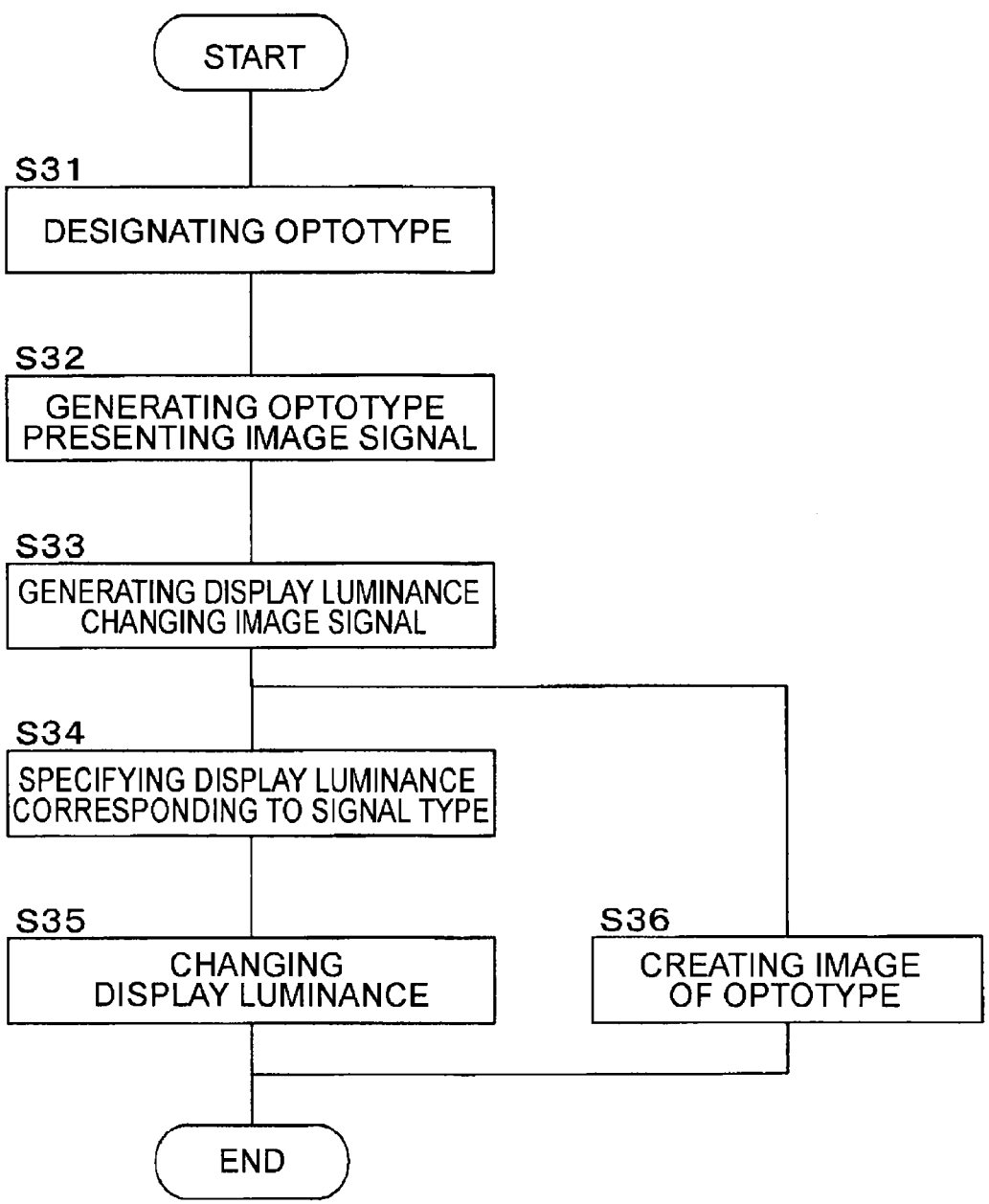
FIG. 9 is a flowchart illustrating an example of operation of an optotype presenting apparatus according to an embodiment.

An operation of the optotype presenting apparatus 1 according to the present embodiment is described. An example of an operation of the optotype presenting apparatus 1 is shown in FIG. 9.

S31: Designating Optotype

Once the user uses the operation part 10 to designate an optotype, the operation part 10 transmits an operation signal indicating the type of the designated optotype to the image signal generator 20.

S32: Generating Optotype Presenting Image Signal

The image signal generator 20 generates an optotype presenting image signal corresponding to the type of the optotype indicated by the operation signal based on the operation signal input from the operation part 10. The image signal generator 20 transmits the generated optotype presenting image signal to the controller 30.

S33: Generating Display Luminance Changing Image Signal

The image signal generator 20 generates a display luminance changing image signal corresponding to the type of the optotype indicated by the operation signal based on the operation signal input from the operation part 10. The image signal generator 20 transmits the generated display luminance changing image signal to the controller 30.

S34: Specifying Display Luminance Corresponding to Signal Type

The image analyzer 31 or the backlight controller 33 specifies display luminance corresponding to the signal type of the display luminance changing image signal from the image signal generator 20 based on the signal type/display luminance associating information.

S35: Changing Display Luminance

The backlight controller 33 controls the backlight 43 based on the display luminance specified in Step S34, thereby changing display luminance of the display 40 to the specified display luminance.

S36: Creating Image of Optotype

The image creation controller 32 controls the image creating part 42 based on the optotype presenting image signal input from the image signal generator 20 to create an image of the pattern of the optotype.

This completes processing of changing display luminance of the optotype according to the present operation example. From such processing, display luminance is changed by the change amount corresponding to the type of the optotype designated. The user performs examinations of eyes by using the optotype thus presented.

[Effects]

Effects of the optotype presenting apparatus 1 of the present embodiment are explained.

The image signal generator 20 of the present embodiment separately generates two kinds of image signals, namely the optotype presenting image signal and the display luminance changing image signal. The controller 30 displays the optotype on the display 40 based on the generated optotype presenting image signal and changes display luminance of the display 40 based on the display luminance changing image signal.

According to the optotype presenting apparatus 1 thus configured, it is possible to present an optotype(s) for a left eye and an optotype for a right eye with suitable brightness (display luminance) in accordance with the type(s) of the optotype(s). Consequently, examinations of eyes may be carried out accurately.

A configuration may be applied in which the image signal generator 20 generates two or more types of display luminance changing image signals in accordance with types of optotypes and the controller 30 changes display luminance based on the type of the generated display luminance changing image signal. Alternatively, the controller 30 may change display luminance by a change amount corresponding to the type of the display luminance changing image signal.

The optotype presenting apparatus 1 may further include the operation part 10 for designating a type of an optotype to be displayed on the display 40. In this case, the operation part 10 functions as an example of an "optotype type designating part". The image signal generator 20 is configured to generate an image signal corresponding to the type of the optotype designated via the operation part 10.

Fourth Embodiment

An optotype presenting apparatus according to the fourth embodiment changes display luminance by using a signal (display luminance changing signal) other than image signals, and is configured to transmit the display luminance changing signal from an operation device (remote controller etc.) that receives instructions by an user to a display device directly.

[Configuration]

Figure 10:
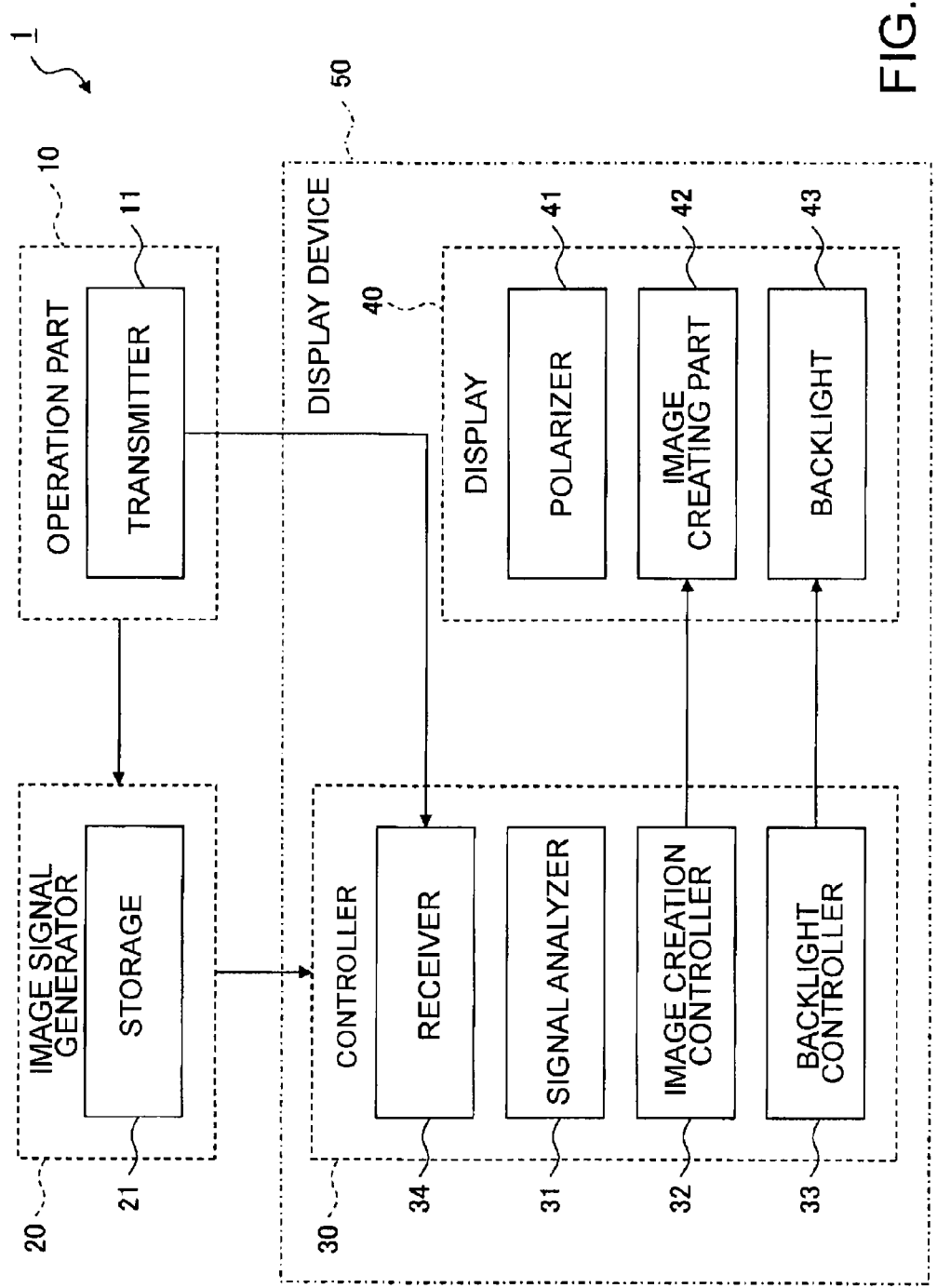
FIG. 10 is a schematic diagram illustrating an example of a configuration of an optotype presenting apparatus according to an embodiment.

FIG. 10 illustrates an example of a configuration of the optotype presenting apparatus according to the present embodiment. In this optotype presenting apparatus 1, the controller 30 and the display 40 are provided with a display device 50. The display device 50 is a flat panel display such as a liquid crystal display, for example.

The operation part 10 is a remote controller. The operation part 10 includes a transmitter 11 that has a function of transmitting signals to the image signal generator 20 as in the first embodiment and communicates with a receiver 34 of the display device 50. A method of communication may be wire communication or wireless communication. The transmitter 11 transmits a signal (display luminance changing signal) including display luminance information corresponding to the type of the optotype designated via the operation part 10. The receiver 34 receives this display luminance changing signal.

Processing of generating the display luminance information corresponding to the type of the optotype designated may be carried out as in the first embodiment. This processing may be executed by the image signal generator 20 or the controller 30. In the former case, a microprocessor in the image signal generator 20 executes this processing. In the latter case, the image signal generator 20 generates predetermined information indicating the type of the optotype based on the operation signal input from the operation part 10 and the display luminance information corresponding to this type of the optotype is generated on the display device 50 side. The difference between the former processing and the latter processing is merely whether the display luminance information corresponding to the designated type of the optotype is generated by the image signal generator 20 or the controller 30; therefore, these processing are substantially the same. Consequently, the present embodiment includes the both processing described above.

The receiver 34 transmits the received display luminance changing signal to the backlight controller 33. The backlight controller 33 controls the backlight 43 based on this display luminance changing signal to change display luminance as in the first embodiment. Meanwhile, the operation part 10 transmits an operation signal indicating the designated type of the optotype to the image signal generator 20. The image signal generator 20 generates an optotype presenting image signal corresponding to the designated type of the optotype indicated by this operation signal and transmits it to the controller 30. The image creation controller 32 controls the image creating part 42 based on this optotype presenting image signal to create an image of the pattern of this optotype.

[Operation]

Figure 11:
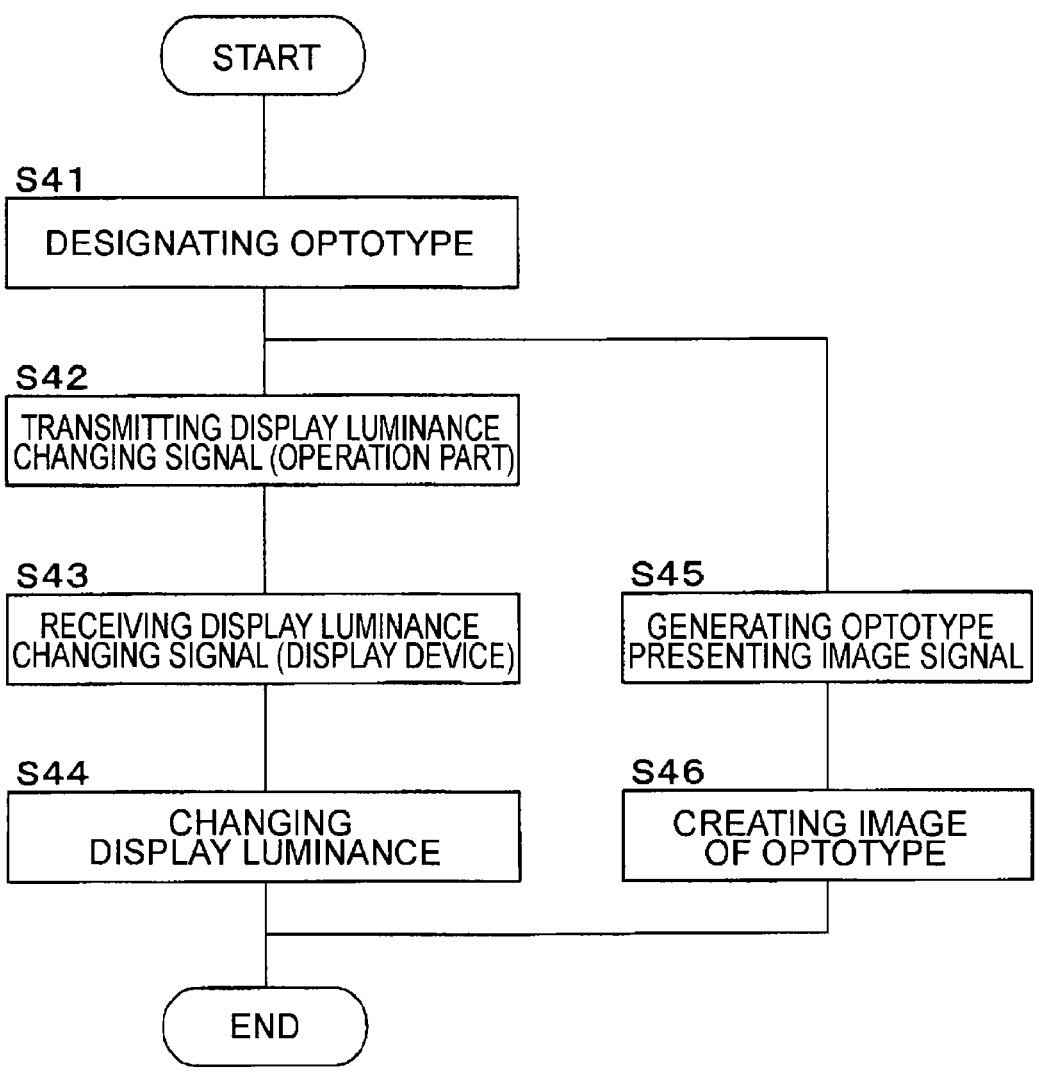
FIG. 11 is a flowchart illustrating an example of operation of an optotype presenting apparatus according to an embodiment.

An operation of the optotype presenting apparatus 1 according to the present embodiment is described. An example of an operation of the optotype presenting apparatus 1 is shown in FIG. 11.

S41: Designating Optotype

Once the user uses the operation part 10 to designate an optotype, the operation part 10 transmits an operation signal indicating the type of the designated optotype to the image signal generator 20.

S42: Transmitting Display Luminance Changing Signal

Simultaneously with transmission of the operation signal (or before or after the transmission), the operation part 10 generates display luminance information corresponding to the designated type of the optotype and transmits a display luminance changing signal including this display luminance information by the transmitter 11.

S43: Receiving Display Luminance Changing Signal

The receiver 34 of the controller 30 receives the display luminance changing signal transmitted from the operation part 10. The signal analyzer 31 analyzes this display luminance changing signal to extract the display luminance information.

S44: Changing Display Luminance

The backlight controller 33 controls the backlight 43 based on the display luminance information extracted by the signal analyzer 31 to change display luminance.

S45: Generating Optotype Presenting Image Signal

Meanwhile, the image signal generator 20 receives the operation signal transmitted from the operation part 10 in Step S41 and generates an optotype presenting image signal corresponding to the type of the optotype indicated by the operation signal. The image signal generator 20 transmits the generated optotype presenting image signal to the controller 30.

S46: Creating Image of Optotype

The image creation controller 32 controls the image creating part 42 based on the optotype presenting image signal input from the image signal generator 20 to create an image of the pattern of the optotype.

This completes processing of changing display luminance of the optotype according to the present operation example. From this processing, display luminance is changed by a change amount in accordance with the designated type of optotype. The user performs examinations of eyes by using the optotype thus presented.

[Effects]

Effects of the optotype presenting apparatus 1 of the present embodiment are explained.

The optotype presenting apparatus 1 includes the operation part 10 for designating the type of the optotype to be displayed on the display 40. The operation part 10 includes the transmitter 11 that transmits a signal (display luminance changing signal) including display luminance information indicating display luminance corresponding to the designated type of the optotype. The controller 30 includes the receiver 34 that receives the signal transmitted from the transmitter 11. Further, the controller 30 changes display luminance of the display 40 based on the signal received by the receiver 34 and displays an optotype corresponding to the designated type of optotype on the display 40.

According to the optotype presenting apparatus 1 thus configured, it is possible to present an optotype(s) for a left eye and an optotype for a right eye with suitable brightness (display luminance) in accordance with the type(s) of the optotype(s). Consequently, examinations of eyes may be carried out accurately.

Fifth Embodiment

An optotype presenting apparatus according to the fifth embodiment changes display luminance by using a signal (display luminance changing signal) other than image signals, and is configured to transmit the display luminance changing signal from a device that has received an operation signal from an operation device to a display device.

[Configuration]

Figure 12:
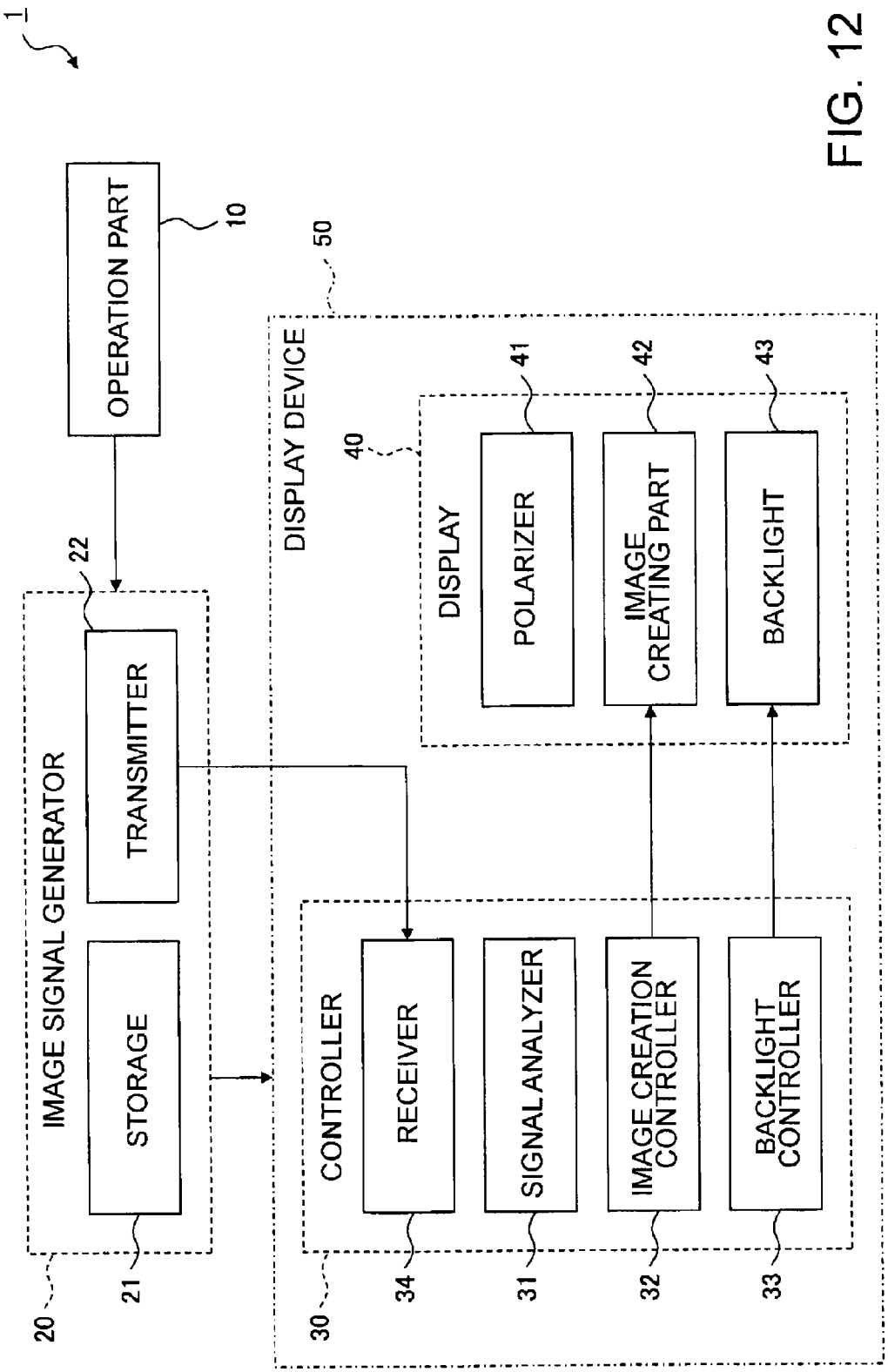
FIG. 12 is a schematic diagram illustrating an example of a configuration of an optotype presenting apparatus according to an embodiment.

FIG. 12 illustrates an example of a configuration of the optotype presenting apparatus according to the present embodiment. In this optotype presenting apparatus 1, the controller 30 and the display 40 are provided with a display device 50 as in the fourth embodiment.

The image signal generator 20 includes a transmitter 22 that communicates with the receiver 34 of the display device 50 in addition to the storage 21 similar to the first embodiment. A method of communication may be wire communication or wireless communication. Wireless communication may be any type such as infrared data communication, wireless LAN, Bluetooth (registered trademark), etc. The transmitter 11 transmits a signal (display luminance changing signal) including display luminance information corresponding to the type of the optotype designated via the operation part 10. The receiver 34 receives this display luminance changing signal.

Processing of generating the display luminance information corresponding to the designated type of the optotype may be carried out as in the first embodiment. This processing may be executed by the operation part 10 or the controller 30. In the former case, a microprocessor in the operation part 10 executes this processing. In the latter case, the operator 10 generates information indicating the designated type of the optotype and the display luminance information corresponding to this type of the optotype is generated on the display device 50 side. The difference between the former processing and the latter processing is merely whether the display luminance information corresponding to the designated type of the optotype is generated by the operation part 10 or the controller 30; therefore, these processing are substantially the same. Consequently, the present embodiment includes the both processing described above.

The receiver 34 transmits the received display luminance changing signal to the backlight controller 33. The backlight controller 33 controls the backlight 43 based on this display luminance changing signal to change display luminance as in the first embodiment. Meanwhile, the operation part 10 transmits an operation signal indicating the designated type of the optotype to the image signal generator 20. The image signal generator 20 generates an optotype presenting image signal corresponding to the designated type of the optotype indicated by this operation signal and transmits it to the controller 30. The image creation controller 32 controls the image creating part 42 based on this optotype presenting image signal to create an image of the pattern of this optotype.

[Operation]

Figure 13:
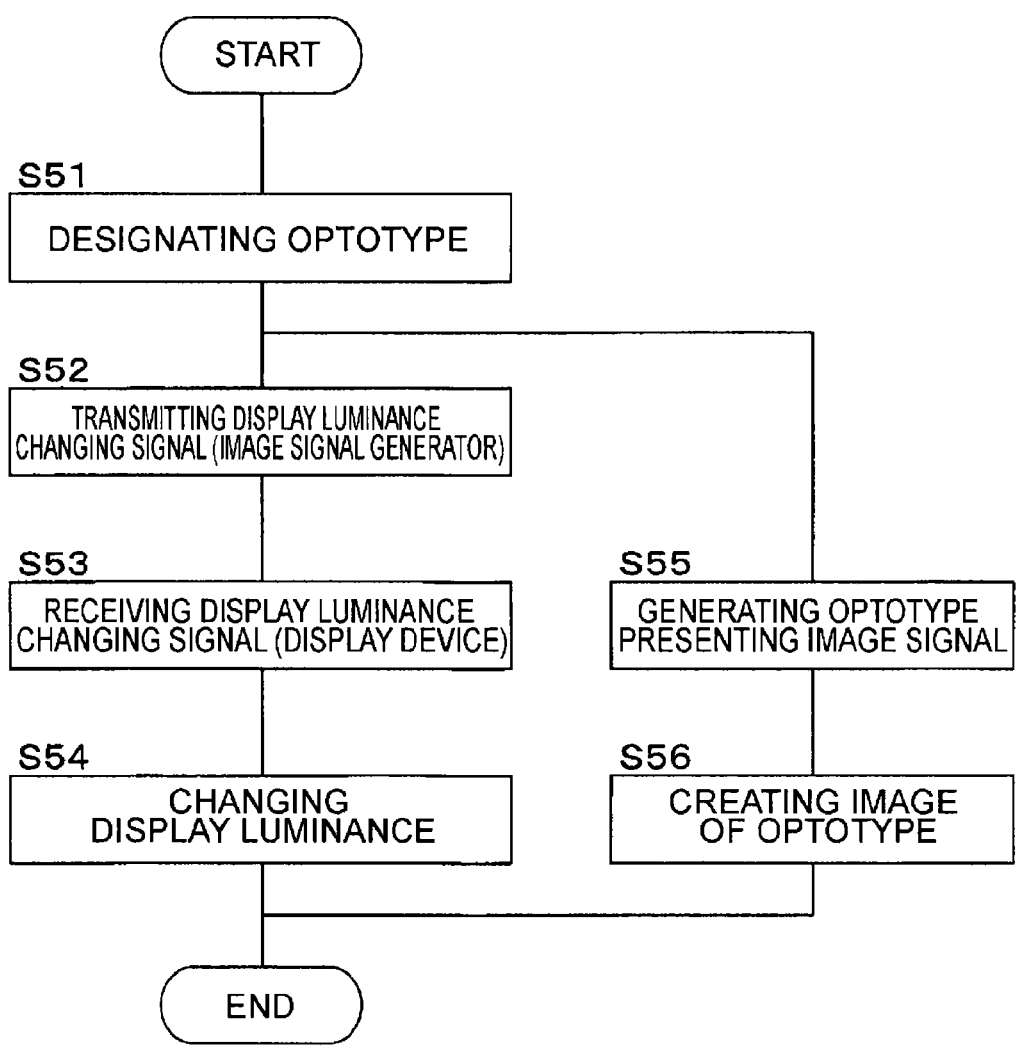
FIG. 13 is a flowchart illustrating an example of operation of an optotype presenting apparatus according to an embodiment.

An operation of the optotype presenting apparatus 1 according to the present embodiment is described. An example of an operation of the optotype presenting apparatus 1 is shown in FIG. 13.

S51: Designating Optotype

Once the user uses the operation part 10 to designate an optotype, the operation part 10 transmits an operation signal indicating the type of the designated optotype to the image signal generator 20.

S52: Transmitting Display Luminance Changing Signal

The image signal generator 20 generates display luminance information corresponding to the designated type of the optotype based on this operation signal and transmits a display luminance changing signal including this display luminance information by the transmitter 22.

S53: Receiving Display Luminance Changing Signal

The receiver 34 of the controller 30 receives the display luminance changing signal transmitted from the image signal generator 20. The signal analyzer 31 analyzes this display luminance changing signal to extract the display luminance information.

S54: Changing Display Luminance

The backlight controller 33 controls the backlight 43 based on the display luminance information extracted by the signal analyzer 31 to change display luminance.

S55: Generating Optotype Presenting Image Signal

Simultaneously with transmission of the display luminance changing signal (S52) (or before or after the transmission), the image signal generator 20 generates an optotype presenting image signal corresponding to the type of the optotype indicated by the operation signal from the operation part 10. The image signal generator 20 transmits the generated optotype presenting image signal to the controller 30.

S56: Creating Image of Optotype

The image creation controller 32 controls the image creating part 42 based on the optotype presenting image signal input from the image signal generator 20 to create an image of the pattern of the optotype.

This completes processing of changing display luminance of the optotype according to the present operation example. From this processing, display luminance is changed by a change amount in accordance with the designated type of optotype. The user performs examinations of eyes by using the optotype thus presented.

[Effects]

Effects of the optotype presenting apparatus 1 of the present embodiment are explained.

The optotype presenting apparatus 1 includes the operation part 10 for designating the type of the optotype to be displayed on the display 40 and the image signal generator 20 that generates the image signal for displaying the designated type of the optotype. The image signal generator 20 includes the transmitter 22 that transmits a signal including display luminance information indicating display luminance corresponding to the designated type of the optotype. The controller 30 includes the receiver 34 that receives the signal transmitted from the image signal generator 20. Then, the controller 30 changes display luminance based on the signal received by the receiver 34 and displays an optotype based on the image signal generated by the image signal generator 20.

According to the optotype presenting apparatus 1 thus configured, it is possible to present an optotype(s) for a left eye and an optotype for a right eye with suitable brightness (display luminance) in accordance with the type(s) of the optotype(s). Consequently, examinations of eyes may be carried out accurately.

Sixth Embodiment

An optotype presenting apparatus according to the sixth embodiment changes display luminance based on information other than types of optotypes, and is configured to change display luminance according to types of examinations of eyes.

Examples of examinations carried out by displaying high luminance optotypes include the followings. Firstly, examples of monocular tests with both eyes open include visual acuity test, red-green test, astigmatism test, cross cylinder test, etc. Further, examples of binocular tests include polarization red-green balance test, polarization binocular balance test, polarization cross heterophoria test, polarization fixation disparity test, polarization rotation heterophoria test, polarization aniseikonia test, polarization stereopsis, etc.

[Configuration]

An optotype presenting apparatus according to the present embodiment includes configurations similar to the first embodiment, for example. In the following, FIG. 1 is referred to for explanation. The operation part 10 is used for designating examination types. The operation part 10 is an example of an "examination type designating part".

It should be noted that there are cases in which the same examination as before is carried out again such as preoperative-postoperative observation and follow up observation. In such cases, it is possible to refer to an electronic medical record of a concerned patient and automatically designate the examination type. This processing is carried out by the controller 30, for example. Similarly, in cases in which examination types to be applied are determined in advance such as health check and clinical path, it is possible to refer to examination types determined in advance and automatically designate them.

Further, when a plurality of examinations is carried out and when the order of examinations is determined in advance, it is possible to automatically designate the examinations successively according to the order. In contrast, when the order of examinations is not determined in advance, a list of the examinations may be presented to the user, thereby facilitating an operation of designating examination types. The same applies to cases in which a plurality of optotypes is used in a single examination.

The storage 21 of the image signal generator 20 previously stores examination type/optotype type associating information in which examination types and types of optotypes are associated with each other. This associating information is table information in which each examination type and (one or more) optotype(s) used for the concerned examination type are associated with each other, for example.

[Operation]

Figure 14:
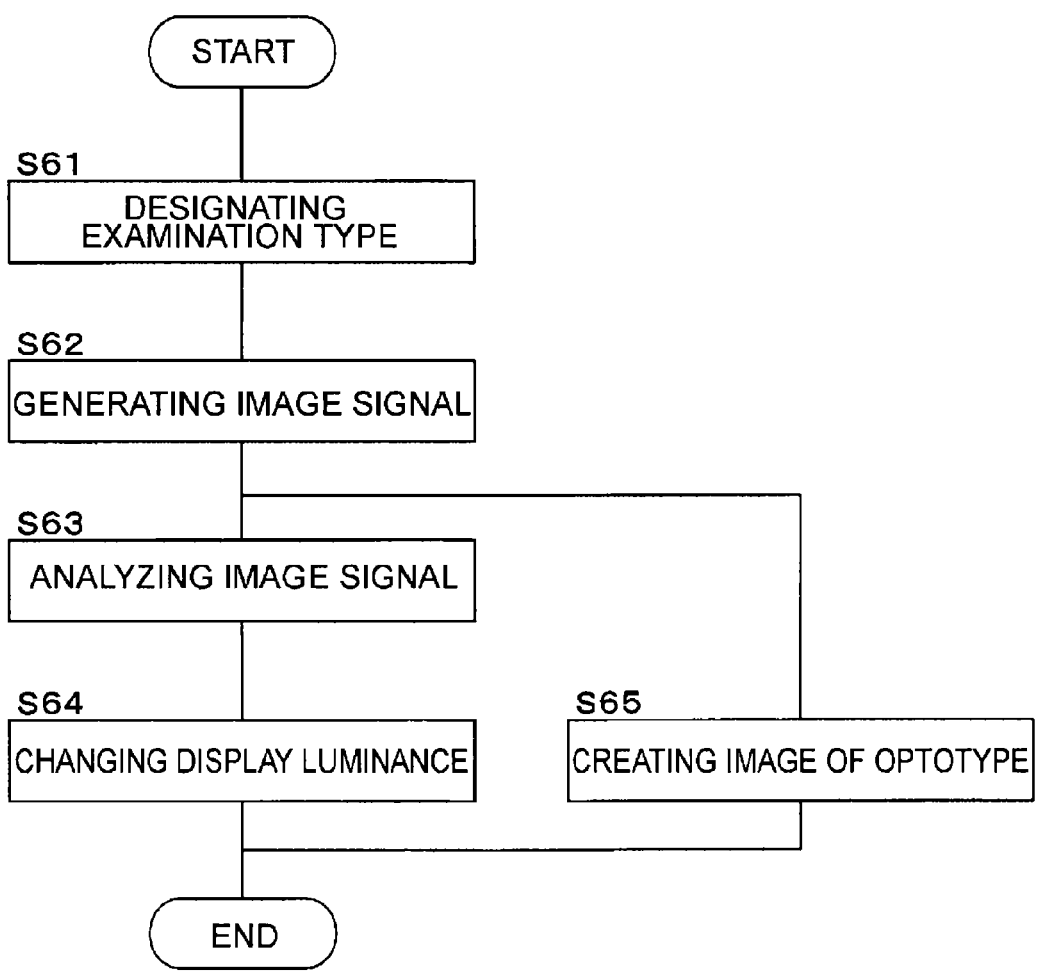
FIG. 14 is a flowchart illustrating an example of operation of an optotype presenting apparatus according to an embodiment.

An operation of the optotype presenting apparatus 1 according to the present embodiment is described. An example of an operation of the optotype presenting apparatus 1 is shown in FIG. 14.

S61: Designating Examination Type

Once the user uses the operation part 10 to designate an examination type, the operation part 10 transmits an operation signal indicating the examination type to the image signal generator 20.

S62: Generating Image Signal

The image signal generator 20 specifies an optotype(s) corresponding to the examination type indicated by the operation signal input from the operation part 10 based on the examination type/optotype type associating information. Further, the image signal generator 20 generates an optotype presenting image signal corresponding to the type(s) of the specified optotype(s). This optotype presenting image signal includes display luminance information indicating display luminance corresponding to the type(s) of the optotype(s). The image signal generator 20 transmits the generated optotype presenting image signal to the controller 30.

S63: Analyzing Image Signal

The image analyzer 31 analyzes the optotype presenting image signal input from the image signal generator 20 to extract the display luminance information (or to judge presence or absence of the display luminance information). The image analyzer 31 transmits the extracted display luminance information (or information indicating presence or absence of the display luminance information) to the backlight controller 33.

S64: Changing Display Luminance

The backlight controller 33 controls the backlight 43 based on the information input from the image analyzer 31 to change display luminance of the display 40.

S65: Creating Image of Optotype

While carrying out Steps 63 and 64, the image creation controller 32 controls the image creating part 42 of the display 40 based on the optotype presenting image signal input from the image signal generator 20 to create an image of the pattern of the optotype.

This completes processing of changing display luminance of the optotype according to the present operation example. The user performs examinations of eyes by using the optotype thus presented.

It should be noted that this operation example is realized by replacing the processing of designating types of optotypes in the first embodiment with the processing of designating examination types. Such replacement may be applied to the second to fifth embodiments. In this case, examination type/optotype type associating information like the present embodiment is prepared.

[Effects]

Effects of the optotype presenting apparatus 1 of the present embodiment are explained.

The optotype presenting apparatus 1 includes the operation part 10 for designating examination types (examination type designating part). The controller 30 displays an optotype(s) corresponding to the designated examination type and changes display luminance based on this examination type.

According to the optotype presenting apparatus 1 thus configured, it is possible to present an optotype(s) for a left eye and an optotype for a right eye with suitable brightness (display luminance) in accordance with the designated examination type. Consequently, examinations of eyes may be carried out accurately.

Seventh Embodiment

An optotype presenting apparatus according to the seventh embodiment changes display luminance based on information other than types of optotypes, and is configured to change display luminance according to presence or absence of application of an optical member (polarizing member) to eyes.

[Configuration]

Figure 15:
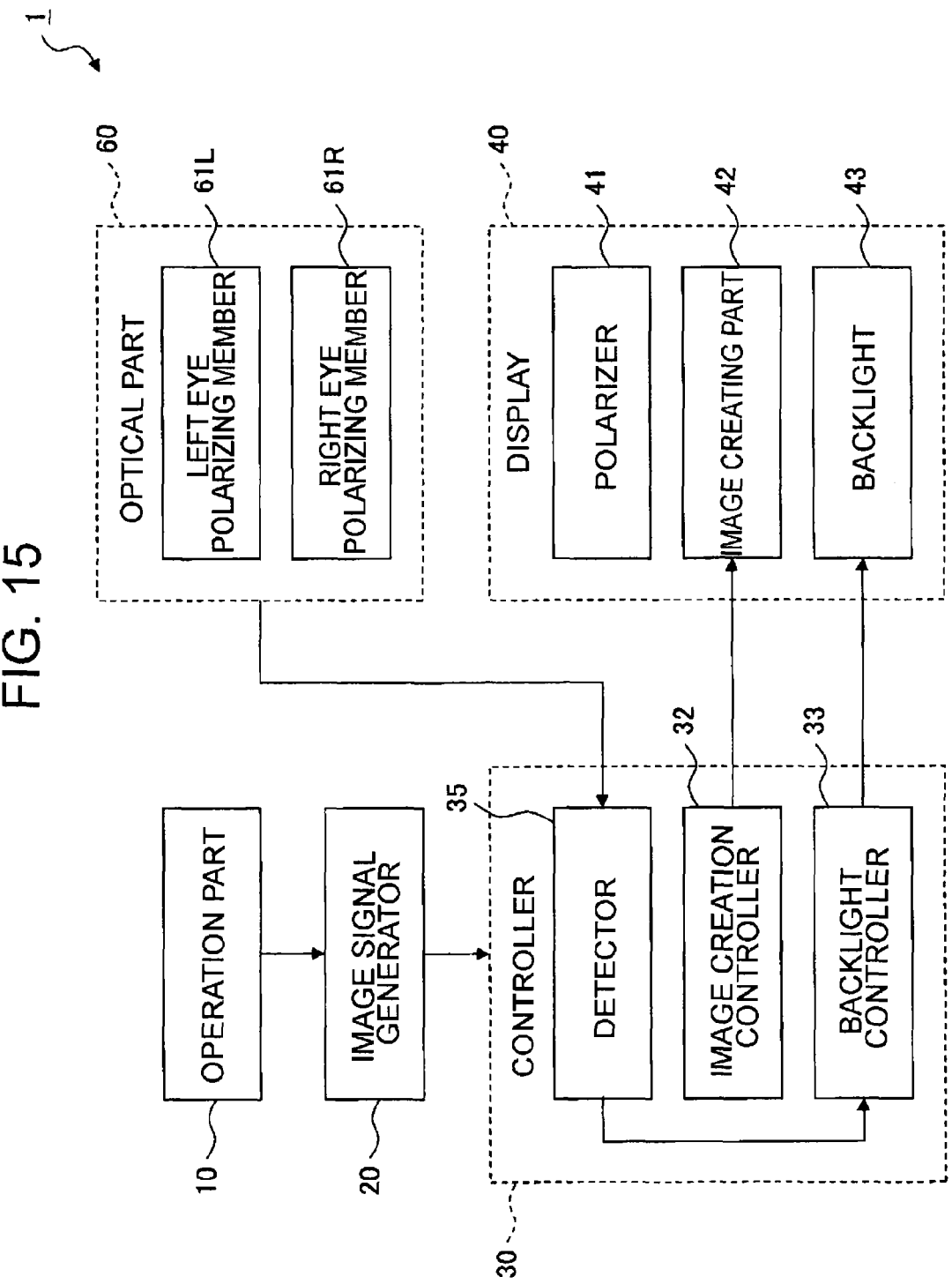
FIG. 15 is a schematic diagram illustrating an example of a configuration of an optotype presenting apparatus according to an embodiment.
Figure 16:
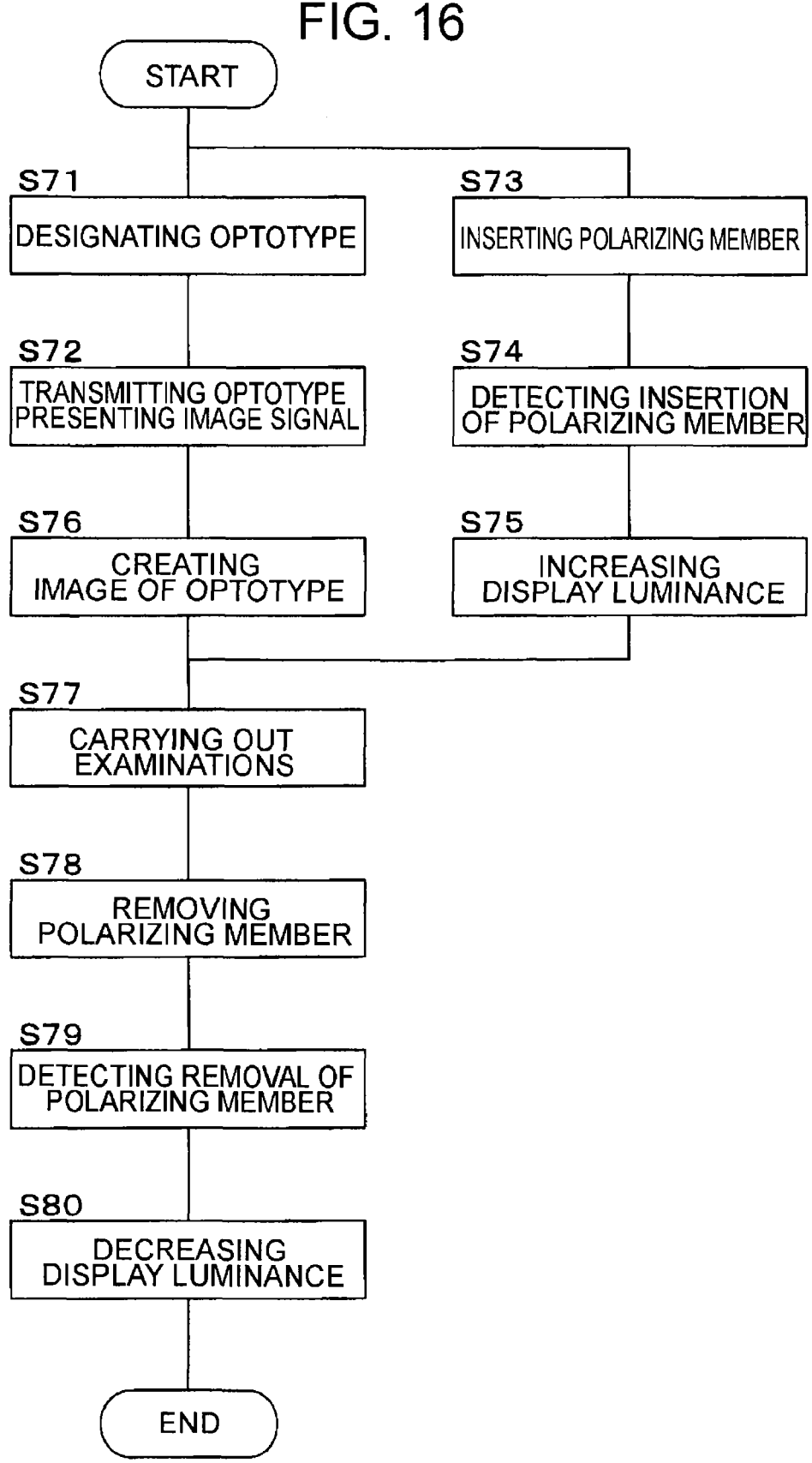
FIG. 16 is a flowchart illustrating an example of operation of an optotype presenting apparatus according to an embodiment.
Figure 17:
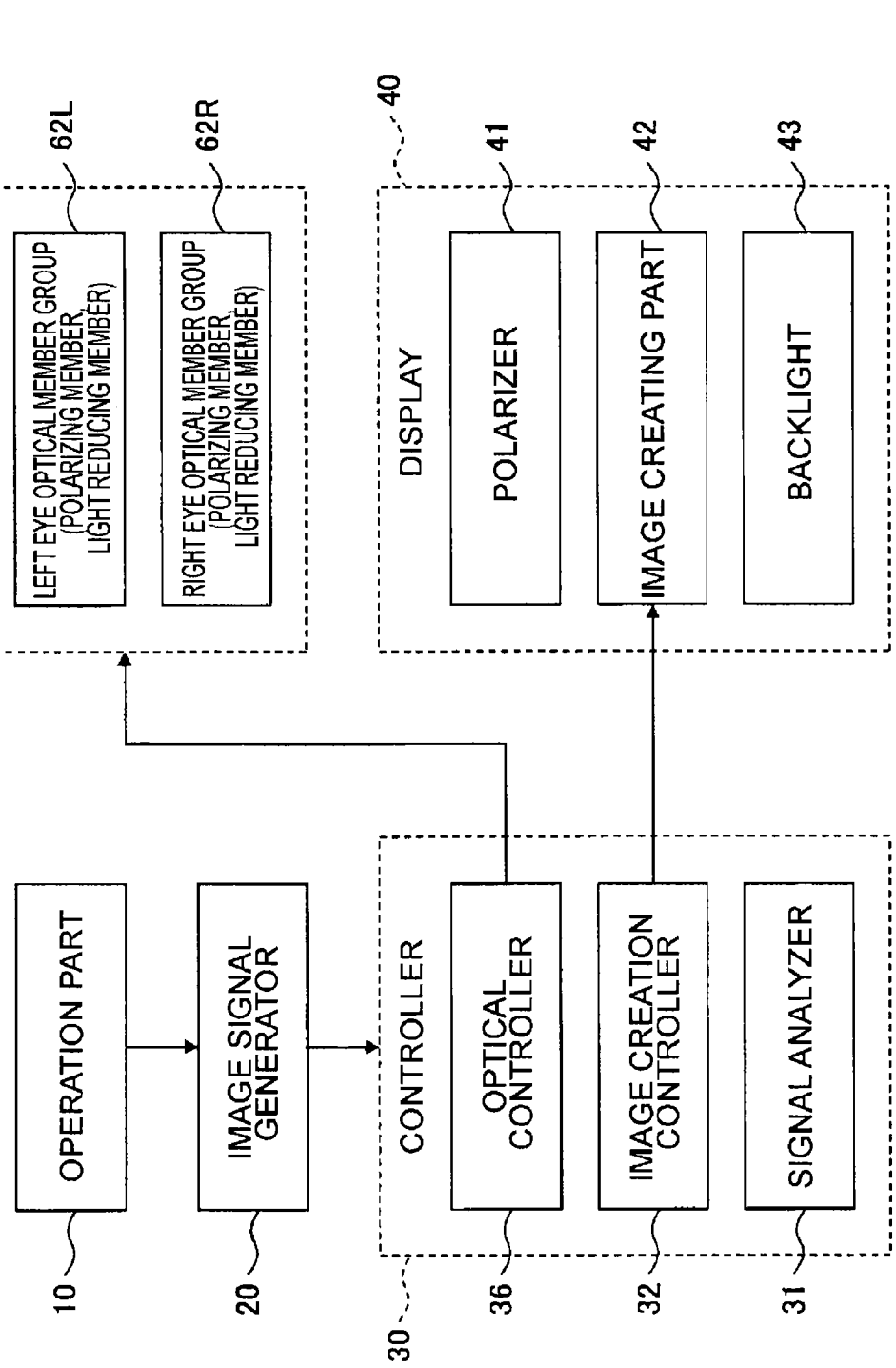
FIG. 17 is a schematic diagram illustrating an example of a configuration of an optotype presenting apparatus according to an embodiment.

FIG. 15 illustrates an example of configuration of an optotype presenting apparatus 1 of the present embodiment. This optotype presenting apparatus 1 includes an optical part 60 in addition to the operation part 10, the image signal generator 20, the controller 30 and the display 40.

The optical part 60 is arranged between the left and right eyes and the display 40, and in particular, arranged just before the left and right eyes. The optical part 60 is provided with various optical members. These optical members are selectively arranged at positions just before the eyes.

As a specific example, left and right turret plates are provided in the optical part 60 and a plurality of optical members is placed in the respective turret plates. Each turret plate is rotatable manually or electrically and the user may rotate the respective turret plates to apply desired optical members to the eyes. Manual rotation may be performed by using operation members (knobs, dials, etc.) provided in the optical part 60, for example. Electrical rotation may be performed by hardware or software provided in the operation part 10, actuators (motors etc.) provided in the optical part 60, and the controller 30 controlling the actuator according to the operation members selected by the operation part 10.

The turret plate for left eyes is provided with a left eye polarizing member 61L having a polarization axis parallel to the polarization axis of the left eye optotype display regions (the first polarization axis) when placed a position just before the left eye. Similarly, the turret plate for right eyes is provided with a right eye polarizing member 61R having a polarization axis parallel to the polarization axis of the right eye optotype display regions (the second polarization axis) when placed a position just before the right eye. The left eye polarizing member 61L and the right eye polarizing member 61R are applied to the left and right eyes when monocular tests or binocular test with both eyes open are carried out by using the high luminance presented optotypes described before.

The controller 30 includes a detector 35 that detects events that the left eye polarizing member 61L and the right eye polarizing member 61R are placed at the positions just before the left and right eyes, respectively. The detector 35 includes a position sensor provided in the optical part, for example. This position sensor may be a rotary encoder that detects rotational positions of the turret plates, or the like. Such a configuration is may be used, in particular, in the case in which optical members to be applied to the eyes are changed manually. On the other hand, in the case in which optical members to be applied to the eyes are changed electrically, the microprocessor in the controller 30 functions as the detector 35 because the controller 30 recognizes selected optical members.

Once detecting the events that the left eye polarizing member 61L and the right eye polarizing member 61R are respectively placed at the positions just before the left and right eyes, the detector 35 transmits a detection signal indicating this fact to the backlight controller 33. The backlight controller 33 controls the backlight 43 to increase display luminance in response to reception of the detection signal from the detector 35.

On the other hand, once detecting the events that the left eye polarizing member 61L and the right eye polarizing member 61R are respectively removed from the positions just before the left and right eyes, the detector 35 transmits a detection signal indicating this fact to the backlight controller 33. The backlight controller 33 receives this detection signal and controls the backlight 43 to decrease display luminance.

It should be noted that display luminance may be controlled by taking designation results of types of optotypes or types of examinations into consideration in addition to the insertion/removal of the left eye polarizing member 61L and the right eye polarizing member 61R with respect to the positions just before the left and right eyes. Control of display luminance based on the designation results of types of optotypes etc. may be any processing described in the above embodiments.

Operation

S71: Designating Optotype

Once the user uses the operation part 10 to designate an optotype, the operation part 10 transmits an operation signal indicating the type of the designated optotype to the image signal generator 20.

S72: Generating Optotype Presenting Image Signal

The image signal generator 20 generates an optotype presenting image signal corresponding to the type of the optotype indicated by the operation signal based on the operation signal input from the operation part 10. The image signal generator 20 transmits the generated optotype presenting image signal to the controller 30.

S73: Inserting Polarizing Member

Simultaneously with or before or after the designation of the type of the optotype (S71), the user places the left eye polarizing member 61L and the right eye polarizing member 61R at positions just before the left and right eyes.

S74: Detecting Insertion of Polarizing Member

The detector 35 detects the events in which the left eye polarizing member 61L and the right eye polarizing member 61R are inserted to the positions just before the left and right eyes, and transmits a detection signal to the backlight controller 33.

S75: Increasing Display Luminance

The backlight controller 33 receives the detection signal and controls the backlight 43 to increase display luminance of the display 40.

S76: Creating Image of Optotype

The image creation controller 32 controls the image creating part 42 based on the optotype presenting image signal input from the image signal generator 20 to create an image of the pattern of the optotype.

S77: Carrying Out Examinations

The user performs examinations of eyes by using the optotype thus presented.

S78: Removing Polarizing Member

After completing the examinations by the use of the optotype, the user removes the left eye polarizing member 61L and the right eye polarizing member 61R from the positions just before the left and right eyes.

S79: Detecting Removal of Polarizing Member

The detector 35 detects the events in which the left eye polarizing member 61L and the right eye polarizing member 61R are removed from the positions just before the left and right eyes, and transmits a detection signal to the backlight controller 33.

S80: Decreasing Display Luminance

The backlight controller 33 receives the detection signal and controls the backlight 43 to decrease display luminance of the display 40. This completes the explanation of this operation example.

[Effects]

Effects of the optotype presenting apparatus 1 of the present embodiment are explained.

The optotype presenting apparatus 1 includes the display 40, the optical part 60 and the controller 30. The optical part 60 includes the left eye polarizing member 61L and the right eye polarizing member 61R. The left eye polarizing member 61L has the polarization axis parallel to the polarization axis of the left eye optotype display regions of the display 40, and the right eye polarizing member 61R has the polarization axis parallel to the polarization axis of the right eye optotype display regions. The controller 30 controls the display 40 to change display luminance in response to the insertion/removal of the left eye polarizing member 61L and the right eye polarizing member 61R with respect to the positions between the display 40 and the eyes.

As described above, the left eye polarizing member 61L and the right eye polarizing member 61R are applied in a case in which one carries out monocular tests or binocular test with both eyes open by the use of high luminance presented optotypes. According to the present embodiment, it is possible to increase display luminance automatically when high luminance presented optotypes are used, thereby capable of carrying out examinations of eyes accurately.

Eighth Embodiment

An optotype presenting apparatus 1 according to the eighth embodiment utilizes light reducing filters (neutral density filters) to change brightness of optotypes visually recognized by a subject instead of changing display luminance as in the first to seventh embodiments. It should be noted that use/disuse of the light reducing filters may be determined based on any trigger described in the first to seventh embodiments, that is, based on types of optotypes, types of examinations (tests) or presence/absence of application of polarizing members to eyes.

[Configuration]

The optotype presenting apparatus 1 includes the operation part 10, the image signal generator 20, the controller 30, the display 40 and the optical part 60 as in the seventh embodiments.

The optical part 60 is provided with a left eye optical member group 62L and a right eye optical member group 62R, each of which includes a plurality of optical members. Each of these optical member groups 62L and 62R is arranged in a turret plate, for example. The plurality of optical members provided in the respective optical member groups 62L and 62R are applied selectively. Configurations for selecting optical members to be applied to the eyes are the same as the configurations for electrical drive described in the seventh embodiment. Specifically, the optical part 60 includes actuators (motors etc.) for selectively applying the plurality of optical members provided in the respective optical member groups 62L and 62R to the eyes.

The left eye optical member group 62L includes the same left eye polarizing member as the seventh embodiment and a left eye light reducing member. The right eye optical member group 62R includes the same right eye polarizing member as the seventh embodiment and a right eye light reducing member. The light reducing members may be configured by light reducing filters, for example. The left eye polarizing member and the left eye light reducing member may be applied to the left eye simultaneously. Similarly, the right eye polarizing member and the right eye light reducing member may be applied to the right eye simultaneously. Such simultaneous applications may be realized by placing the polarizing member and the light reducing member in different turret plates which are arranged in parallel and controlling the respective turret plates individually.

The controller 30 includes the signal analyzer 31, the image creation controller 32 and an optical controller 36. The signal analyzer 31 and the image creation controller 32 have the same functions as in the first to the seventh embodiments. The optical controller 36 controls the actuators in the optical part 60 to apply the plurality of optical members provided in the respective optical member groups 62L and 62R to the eyes selectively.

It should be noted that any one or more among the signal analyzer 31, the backlight controller 33, the receiver 34 and the detector 35 described in the first to the seventh embodiments may be provided. When the backlight controller 33 is provided, it is possible to configure so as to change brightness of optotypes visually recognized by the subject by use of both insertion/removal of the light reducing members into/from the positions just before the eyes and control of display luminance of the display 40. Further, a configuration may be adopted in which a plurality of light reducing members having different transmittances is selectively applied to the eyes. If this is the case, the optical controller 36 execute selection of light reducing members in accordance with the result of designation of the types of optotypes or types of examinations.

[Operation]

An operation of the optotype presenting apparatus 1 according to the present embodiment is described. An example of an operation of the optotype presenting apparatus 1 is shown in FIG. 18. In the following, an operation example analogous to the first embodiment; however, any of the operations of the second to the seventh embodiments may be applied.

S81: Designating Examination Type

Once the user uses the operation part 10 to designate an examination type, the operation part 10 transmits an operation signal indicating the examination type to the image signal generator 20.

S82: Generating Image Signal

The image signal generator 20 generates an optotype presenting image signal corresponding to the type of the specified optotype. This optotype presenting image signal includes light reducing information indicating presence/absence of application of the light reducing members. The light reducing information may be generated by referring to optotype type/light reduction associating information in which types of optotypes and presence/absence of application of the light reducing members are associated with each other, for example. This optotype type/light reduction associating information is previously stored in storage not illustrated. The image signal generator 20 transmits the generated optotype presenting image signal to the controller 30.

S83: Analyzing Image Signal

The image analyzer 31 analyzes the optotype presenting image signal input from the image signal generator 20 to extract the light reducing information. The image analyzer 31 transmits the extracted light reducing information to the optical controller 36.

S84: Insertion/Removal of Polarizing Members and Light Reducing Members

The optical controller 36 controls the optical part 60 (actuators) based on the light reducing information input from the image analyzer 31 to insert or remove the left eye polarizing member and the left eye light reducing member into/from the position just before the left eye and insert or remove the right eye polarizing member and the right eye light reducing member into/from the position just before the right eye. Here, if the light reducing information indicates presence of application of light reducing members, the optical controller 36 inserts the polarizing members and the light reducing members. In contrast, if the light reducing information indicates absence of application of light reducing members, the optical controller 36 removes the polarizing members and the light reducing members.

S85: Creating Image of Optotype

While carrying out Steps 83 and 84, the image creation controller 32 controls the image creating part 42 of the display 40 based on the optotype presenting image signal input from the image signal generator 20 to create an image of the pattern of the optotype.

This completes processing of the present operation example. The user performs examinations of eyes by using the optotype thus presented. It should be noted that in a case in which a configuration of executing insertion/removal of the polarizing members and the light reducing members in accordance with examination types is adopted, or in a case in which a configuration of executing insertion/removal of the polarizing members and the light reducing members in accordance with presence/absence of application of polarizing members to the eyes is adopted, objective processing is executed according to corresponding embodiment(s) described above.

[Effects]

Effects of the optotype presenting apparatus 1 of the present embodiment are explained.

The optotype presenting apparatus 1 includes the display 40, the optical part 60 and the controller 30. The optical part 60 is capable of selectively arranging, at positions between the display 40 and the eyes, a plurality of optical members including the left eye polarizing member, the right eye polarizing member, the left eye light reducing member and the right eye light reducing member. The left eye polarizing member has the polarization axis parallel to the polarization axis of the left eye optotype display regions of the display 40. The right eye polarizing member has the polarization axis parallel to the polarization axis of the right eye optotype display regions. The controller 30 is capable of displaying a plurality of optotypes on the display 40 selectively. Further, the controller 30 controls the optical part 60 based on the types of optotypes to be displayed on the display 40 to insert/remove the left eye polarizing member, the right eye polarizing member, the left eye light reducing member and the right eye light reducing member into/from the positions between the display 40 and the eyes.

According to the present embodiment, it is possible to automatically change brightness of optotypes visually recognized by the subject in accordance with types of optotypes, thereby capable of performing examinations of the eyes accurately.

The following shows a configuration of automatically changing brightness of optotypes visually recognized by the subject in accordance with examination types. This optotype presenting apparatus includes the display 40, the optical part 60, the examination type designating part, and the controller 30. The optical part 60 is configured similarly to the case of considering types of optotypes. The examination type designating part is configured similarly to the sixth embodiment. The controller 30 displays optotypes corresponding to the examination type designated by the examination type designating part. Further, the controller 30 controls the optical part 60 based on this examination type to insert/remove the left eye polarizing member, the right eye polarizing member, the left eye light reducing member and the right eye light reducing member into/from the positions between the display 40 and the eyes.

According to the present embodiment, it is possible to automatically change brightness of optotypes visually recognized by the subject in accordance with examination types, thereby capable of performing examinations of the eyes accurately.

The following shows a configuration of automatically changing brightness of optotypes visually recognized by the subject in accordance with presence/absence of application of polarizing members. This optotype presenting apparatus includes the display 40, the optical part 60, and the controller 30. The optical part 60 is configured similarly to the case of considering types of optotypes. The controller 30 controls the optical part 60 in accordance with insertion/removal of the left eye polarizing member and the right eye polarizing member to insert/remove the left eye light reducing member and the right eye light reducing member into/from the positions between the display 40 and the eyes.

According to the present embodiment, it is possible to automatically change brightness of optotypes visually recognized by the subject in accordance with presence or absence of application of the polarizing members to the eyes, thereby capable of performing examinations of the eyes accurately.

It should be noted that it may be possible to configure so as to automatically execute insertion/removal of polarizing members in accordance with presence/absence of application of the light reducing members to the eyes in an opposite way to the above configuration.

The configurations described above are merely examples for implementing the present invention. Therefore, it is possible to make arbitrary modification (omission, replacement, addition, etc.) within the scope of the present invention.

What is claimed is:

1. An optotype presenting apparatus comprising:
   a display that includes left eye optotype display regions that output light having a first polarization axis and right eye optotype display regions that output light having a second polarization axis orthogonal to the first polarization axis, wherein the left eye optotype display regions and the right eye optotype display regions are alternately arranged along pixel lines; and
   a controller that
      provides at least one visual acuity test configured for a patient with both eyes open by displaying on the display an optotype in only one of the left eye optotype display regions and the right eye optotype display regions for a monocular test and by displaying optotypes in both of the left eye optotype display regions and the right eye optotype display regions for a binocular test,
      controls, based on a type of the optotype displayed in one of the left eye optotype display regions and the right eye optotype display regions, a backlight of the display to change a display luminance of one or more optotypes for the monocular test, and
      controls, based on types of optotypes displayed in both of the left eye optotype display regions and the right eye optotype display regions, the backlight of the display to change a display luminance of one or more optotypes for the binocular test.

2. The optotype presenting apparatus of claim 1, further comprising an operation part for designating a type of an optotype to be displayed on the display,
   wherein the operation part comprises a transmitter that transmits a signal including display luminance information indicating display luminance corresponding to the designated type, and
   the controller comprises a receiver that receives the transmitted signal and the controller executes change of display luminance based on the received signal and displays an optotype corresponding to the designated type.

3. The optotype presenting apparatus of claim 1, further comprising:
   an operation part for designating a type of an optotype to be displayed on the display; and
   an image signal generator that generates an image signal for displaying an optotype of the designated type,
   wherein the image signal generator comprises a transmitter that transmits a signal including display luminance information indicating display luminance corresponding to the designated type, and
   the controller comprises a receiver that receives the transmitted signal and the controller executes change of display luminance based on the received signal and displays an optotype corresponding to the generated image signal.

4. The optotype presenting apparatus of claim 1, wherein the display comprises an image creating part that creates an optotype and the backlight which are provided behind the image creating part, and
   the controller changes emission intensity of the backlight to execute change of display luminance.

5. The optotype presenting apparatus of claim 1, wherein polarizing films that transmit light having the first polarization axis are provided in the left eye optotype display regions, and
   polarizing films that transmit light having the second polarization axis are provided in the right eye optotype display regions.

6. The optotype presenting apparatus of claim 1, wherein the controller adjusts different optotypes displayed on the display to have different luminance values.

7. The optotype presenting apparatus of claim 1, wherein the controller adjusts the luminance value of the one or more optotypes only in an area of the display having the one or more optotypes.

8. An optotype presenting apparatus comprising:
   a display that includes left eye optotype display regions that output light having a first polarization axis and right eye optotype display regions that output light having a second polarization axis orthogonal to the first polarization axis, wherein the left eye optotype display regions and the right eye optotype display regions are alternately arranged along pixel lines;
   an examination type designating part that designates a type of an examination; and
   a controller that
      provides at least one visual acuity test configured for a patient with both eyes open by displaying on the display an optotype in only one of the left eye optotype display regions and the right eye optotype display regions for a monocular test and by displaying optotypes in both of the left eye optotype display regions and the right eye optotype display regions for a binocular test,
      controls, based on a type of the optotype displayed in one of the left eye optotype display regions and the right eye optotype display regions, a backlight of the display to change a display luminance of one or more optotypes for the monocular test, and controls, based on types of optotypes displayed in both of the left eye optotype display regions and the right eye optotype display regions, the backlight of the display to change a display luminance of one or more optotypes for the binocular test.

9. The optotype presenting apparatus of claim 8, wherein the display comprises an image creating part that creates an optotype and the backlight which are provided behind the image creating part, and the controller changes emission intensity of the backlight to execute change of display luminance.

10. An optotype presenting apparatus comprising:

a display that includes left eye optotype display regions that output light having a first polarization axis and right eye optotype display regions that output light having a second polarization axis orthogonal to the first polarization axis, wherein the left eye optotype display regions and the right eye optotype display regions are alternately arranged along pixel lines;

an optical part that is capable of placing a left eye polarizing member having a polarization axis parallel to the first polarization axis and a right eye polarizing member having a polarization axis parallel to the second polarization axis at locations between the display and eyes; and a controller that provides at least one visual acuity test configured for a patient with both eyes open by displaying on the display an optotype in only one of the left eye optotype display regions and the right eye optotype display regions for a monocular test and by displaying optotypes in both of the left eye optotype display regions and the right eye optotype display regions for a binocular test, controls, based on a type of the optotype displayed in one of the left eye optotype display regions and the right eye optotype display regions, a backlight of the display to change a display luminance of one or more optotypes for the monocular test, and controls, based on types of optotypes displayed in both of the left eye optotype display regions and the right eye optotype display regions, the backlight of the display to change a display luminance of one or more optotypes for the binocular test.

11. The optotype presenting apparatus of claim 10, wherein the display comprises an image creating part that creates an optotype and the backlight which are provided behind the image creating part, and the controller changes emission intensity of the backlight to execute change of display luminance.

12. The optotype presenting apparatus of claim 1, further comprising an image signal generator that generates an image signal for displaying an optotype, wherein the image signal includes display luminance information indicating display luminance corresponding to this optotype, wherein the controller displays the optotype based on the generated image signal and executes change of display luminance based on the display luminance information included in this image signal.

13. The optotype presenting apparatus of claim 12, further comprising an optotype type designating part that designates a type of an optotype to be displayed on the display, wherein the image signal generator generates an image signal corresponding to the designated type.

14. The optotype presenting apparatus of claim 1, further comprising an image signal generator that generates a first image signal for displaying an optotype and a second image signal including display luminance information indicating display luminance, wherein the controller displays the optotype based on the first image signal generated and executes change of display luminance based on the second image signal.

15. The optotype presenting apparatus of claim 14, wherein the controller executes change of display luminance based on a time for which the second image signal is received.

16. The optotype presenting apparatus of claim 15, wherein the controller executes change of display luminance when the second image signal is continuously received as long as a preset period.

17. The optotype presenting apparatus of claim 15, wherein the controller changes display luminance by a change amount corresponding to a time length in which the second image signal is continuously received.

18. The optotype presenting apparatus of claim 14, wherein the image signal generator is capable of generating two or more types of second image signals, and the controller executes change of display luminance based on the type of the second image signal generated.

19. The optotype presenting apparatus of claim 18, wherein the controller changes display luminance by a change amount corresponding to the type of the second image signal.

* * * * *